(12) United States Patent
Grenier et al.

(10) Patent No.: US 9,392,757 B2
(45) Date of Patent: Jul. 19, 2016

(54) SUN TRACKING LIGHT DISTRIBUTOR SYSTEM

(71) Applicant: INSTITUT NATIONAL D'OPTIQUE, Québec (CA)

(72) Inventors: Paul Grenier, Québec (CA); Marc Levesque, Saint-Augustin-de-Desmaures (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 361 days.

(21) Appl. No.: 14/095,322

(22) Filed: Dec. 3, 2013

(65) Prior Publication Data

US 2014/0123552 A1    May 8, 2014

Related U.S. Application Data

(63) Continuation-in-part of application No. 13/780,857, filed on Feb. 28, 2013, now abandoned.

(60) Provisional application No. 61/655,517, filed on Jun. 5, 2012.

(51) Int. Cl.
| | |
|---|---|
| *F24J 2/08* | (2006.01) |
| *A01G 33/00* | (2006.01) |
| *C12M 1/00* | (2006.01) |
| *C12M 1/09* | (2006.01) |

(52) U.S. Cl.
CPC .............. *A01G 33/00* (2013.01); *C12M 21/02* (2013.01); *C12M 23/56* (2013.01); *C12M 31/08* (2013.01); *C12M 41/08* (2013.01)

(58) Field of Classification Search
CPC ........................................................ F24J 2/08
USPC ........................................................ 126/698
See application file for complete search history.

(56) References Cited

U.S. PATENT DOCUMENTS

| | | | |
|---|---|---|---|
| 4,088,121 A | 5/1978 | Lapeyre | |
| 4,153,039 A | 5/1979 | Carroll | |
| 5,977,478 A * | 11/1999 | Hibino | F24J 2/06 126/684 |
| 5,981,271 A | 11/1999 | Doucha et al. | |

(Continued)

FOREIGN PATENT DOCUMENTS

| | | |
|---|---|---|
| WO | 2004074423 | 9/2004 |
| WO | 2011099016 A2 | 8/2011 |

OTHER PUBLICATIONS

Zijffers et al., Design Process of an Area-Efficient Photobioreactor, Mar Biotechnol, Feb. 2008, pp. 404-415, Spinger.

*Primary Examiner* — Avinash Savani
(74) *Attorney, Agent, or Firm* — Fasken Martineau Dumoulin LLP

(57) ABSTRACT

A sun-tracking light distributor system for use in one of an open-ended system and a closed photo-bioreactor for a photosynthetic culture having an aqueous liquid is described. The system comprises: two light distribution walls made of a transparent material allowing sunlight to pass therethrough, the two light distribution walls creating an elongated channel with an interior space adapted to receive the sunlight and an exterior surface adapted to be partly immersed in the aqueous liquid in use; and a displacement system operatively connected to at least one of the two light distribution walls, the displacement system being adapted to change an orientation of the at least one of the two light distribution walls to track a solar position with respect to at least one axis.

12 Claims, 36 Drawing Sheets

(56) References Cited

U.S. PATENT DOCUMENTS

| | | |
|---|---|---|
| 8,033,047 B2 | 10/2011 | Rasmussen et al. |
| 8,650,798 B1 | 2/2014 | Armstrong et al. |
| 2005/0028524 A1* | 2/2005 | Laing .................... F24J 2/5267 60/641.8 |
| 2006/0260605 A1* | 11/2006 | Connor .................... F24J 2/085 126/561 |
| 2008/0160591 A1 | 7/2008 | Willson et al. |
| 2008/0311649 A1 | 12/2008 | Cloud et al. |
| 2009/0291485 A1 | 11/2009 | Shigematsu et al. |
| 2009/0305389 A1 | 12/2009 | Willson et al. |
| 2010/0216203 A1 | 8/2010 | Trent et al. |
| 2010/0248333 A1 | 9/2010 | Bartilson |
| 2011/0117631 A1 | 5/2011 | Woerlee et al. |
| 2011/0117632 A1 | 5/2011 | Woerlee et al. |
| 2011/0197317 A1 | 8/2011 | Wong |
| 2013/0029403 A1 | 1/2013 | Hazlebeck et al. |

* cited by examiner

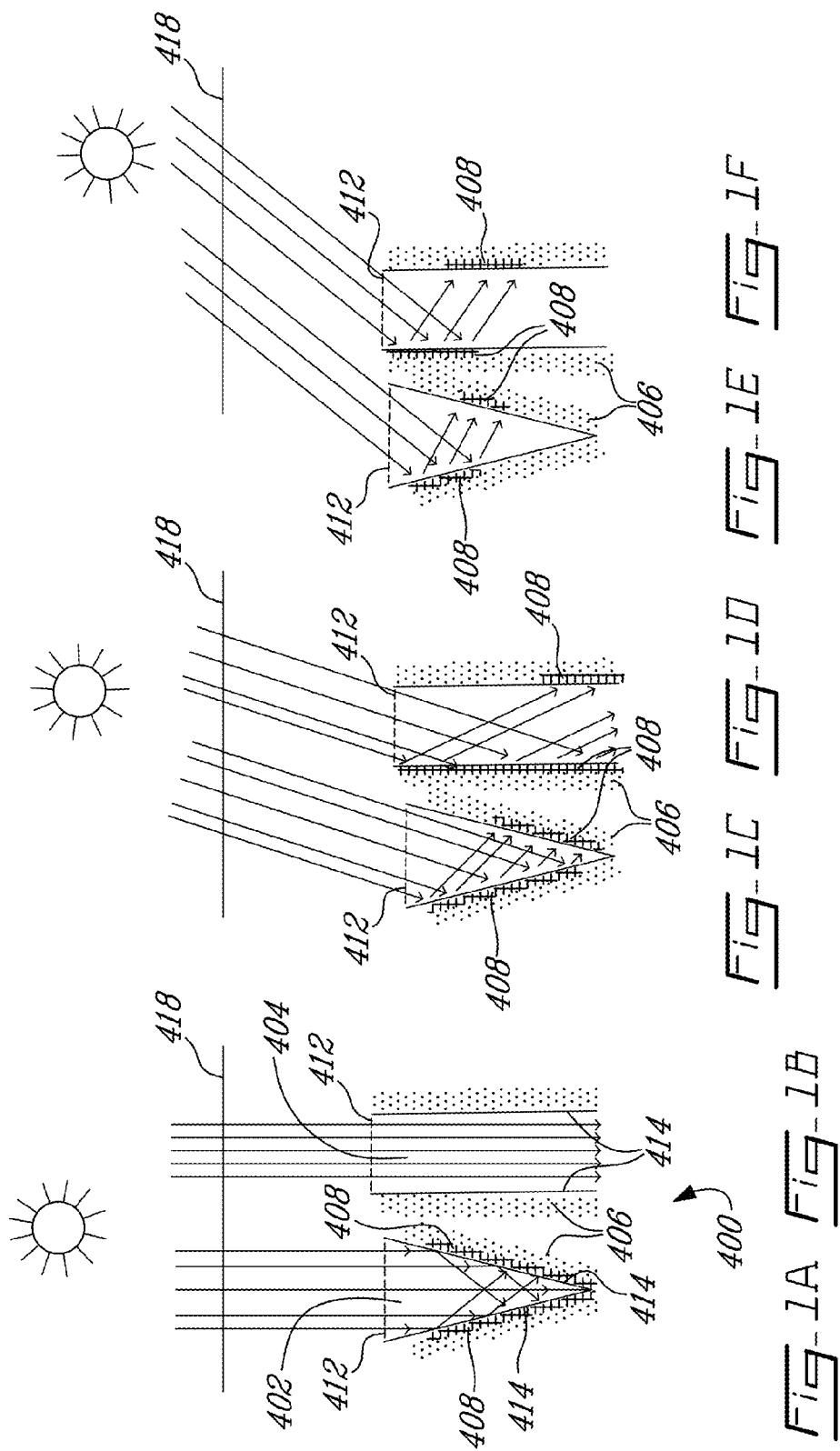

WITHOUT LIGHT DISTRIBUTORS
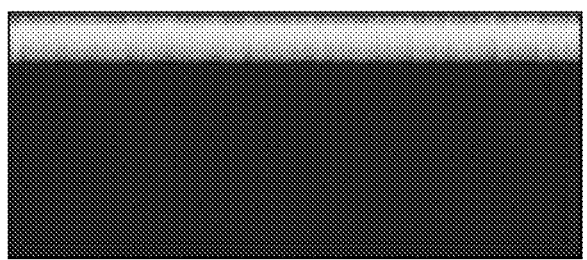
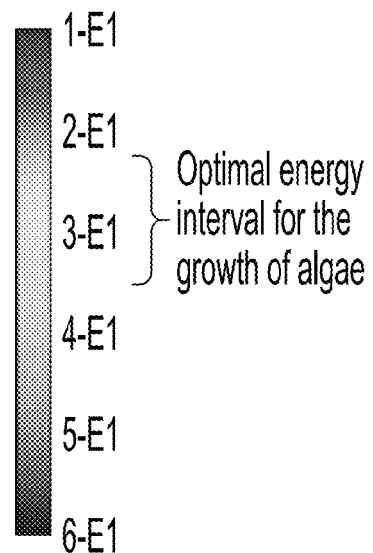
FIG-12A
WITH V-SHAPED LIGHT DISTRIBUTORS
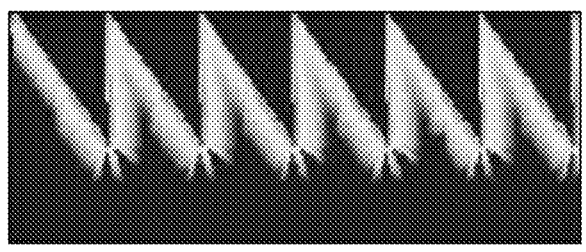
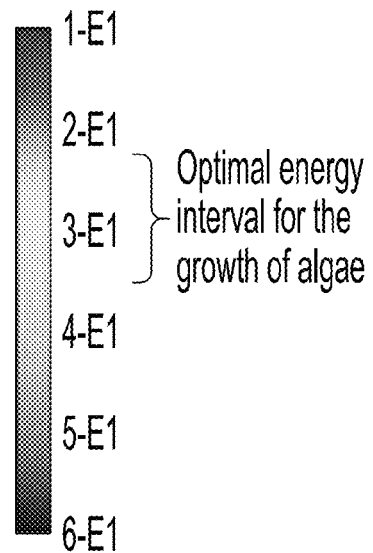
FIG-12B

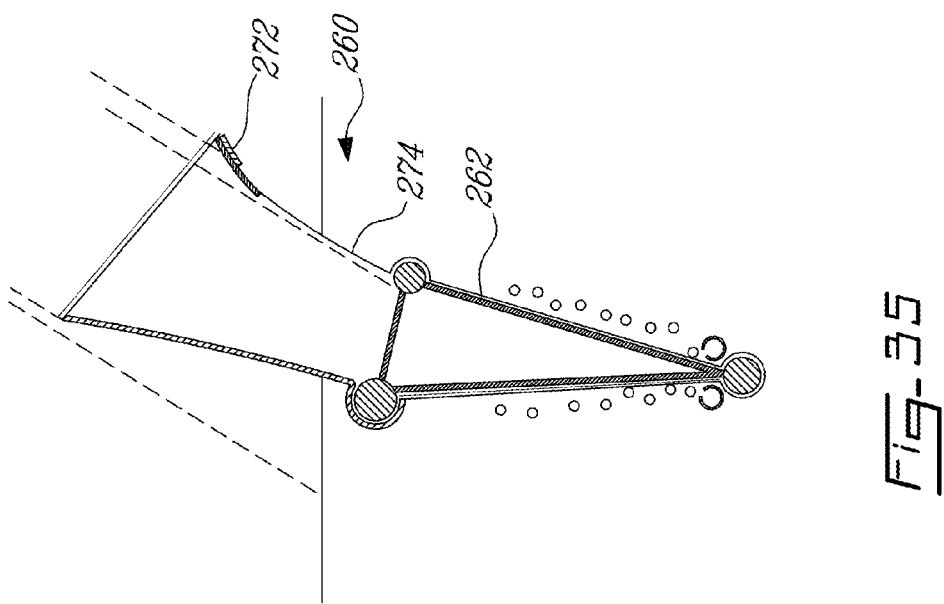

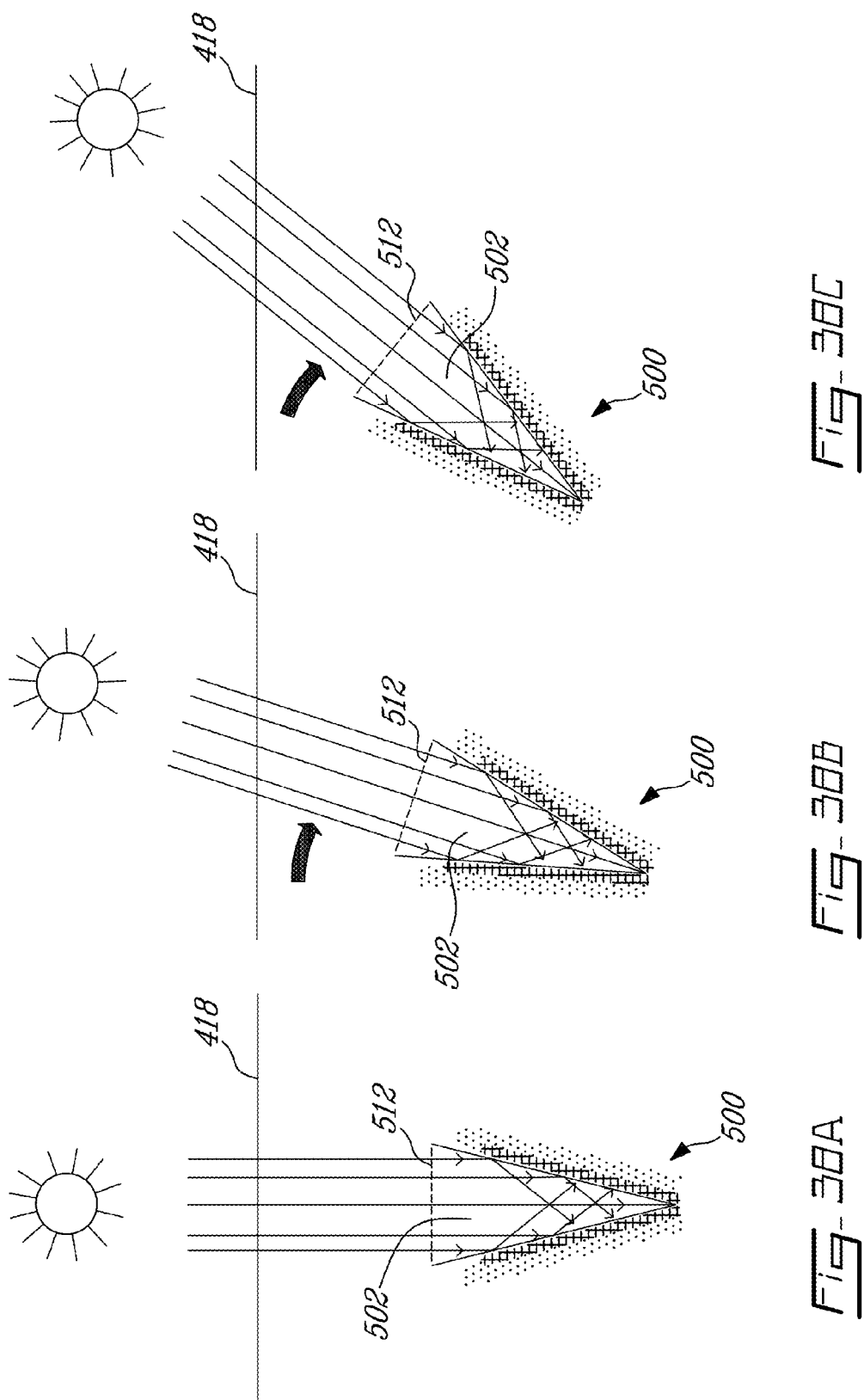

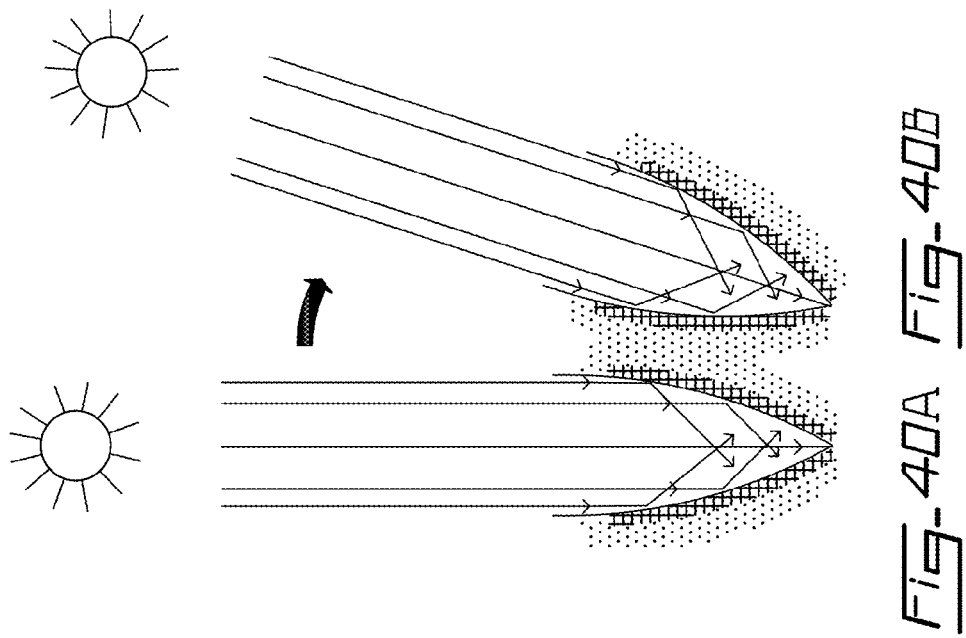
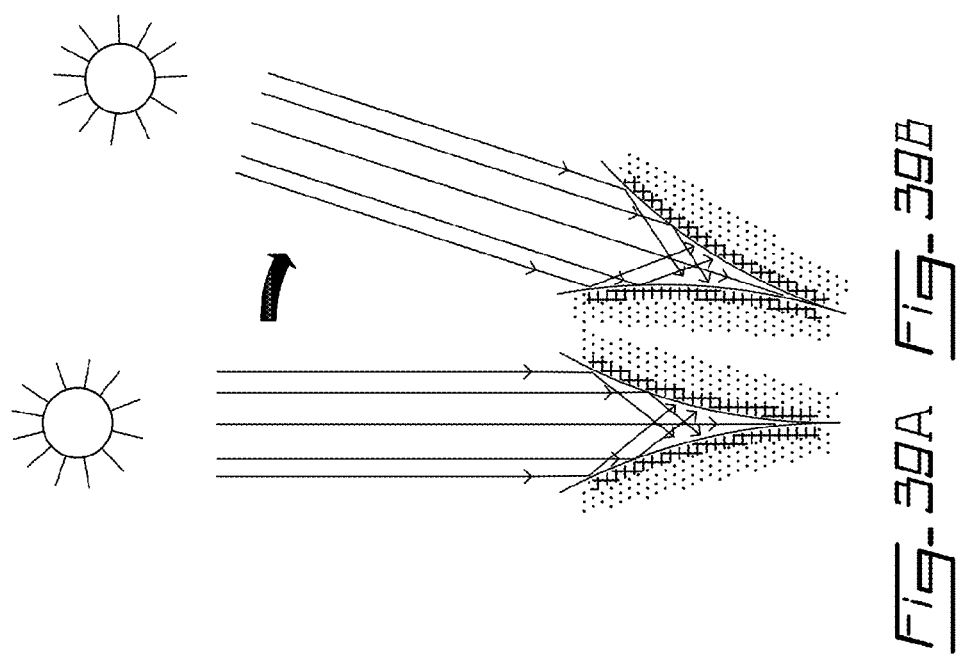

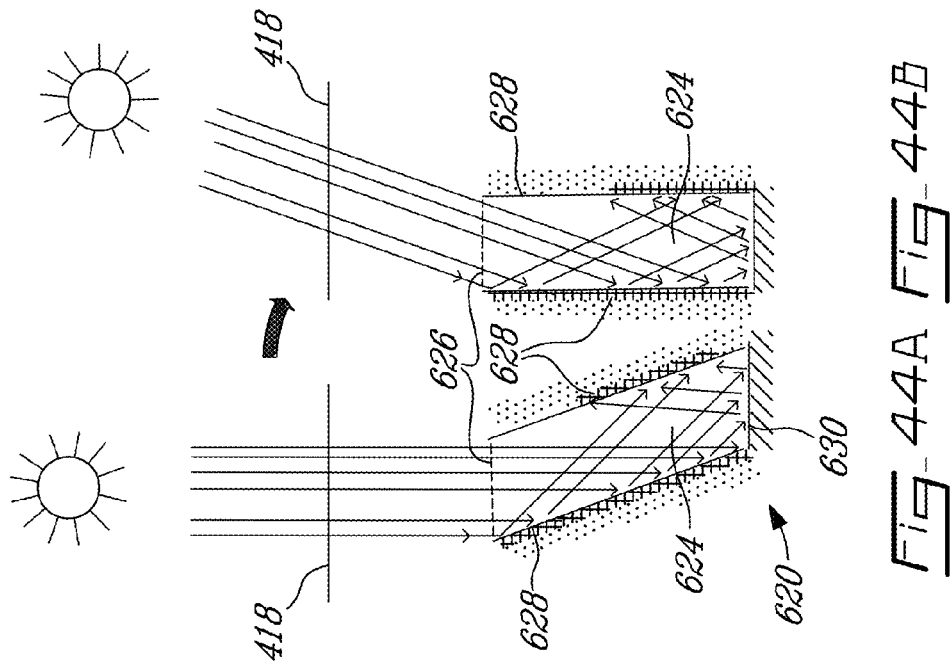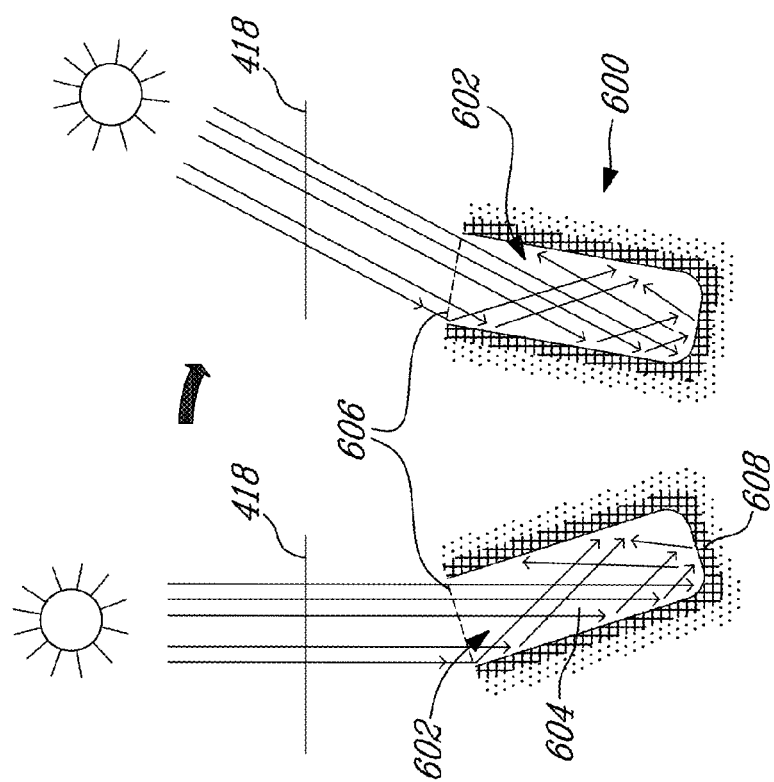

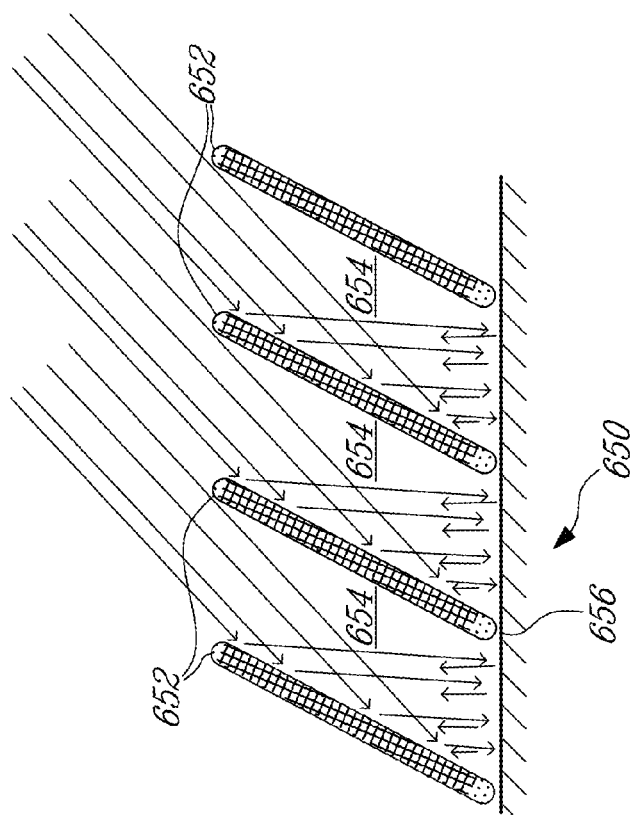
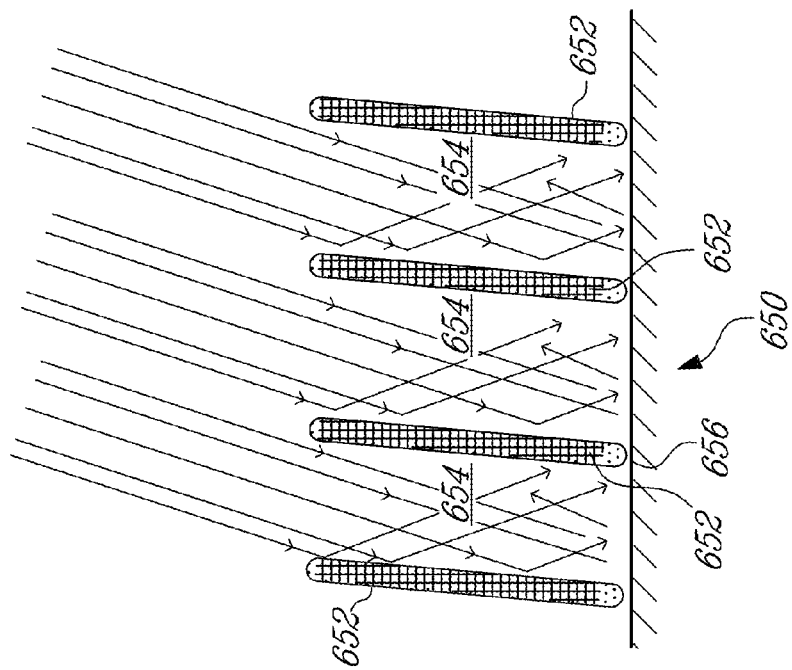

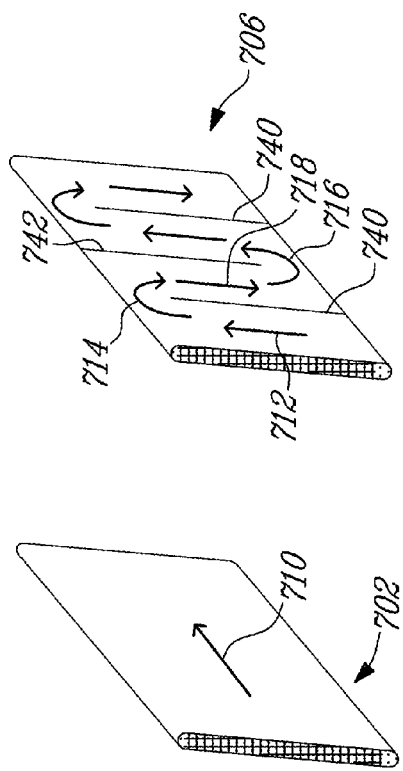
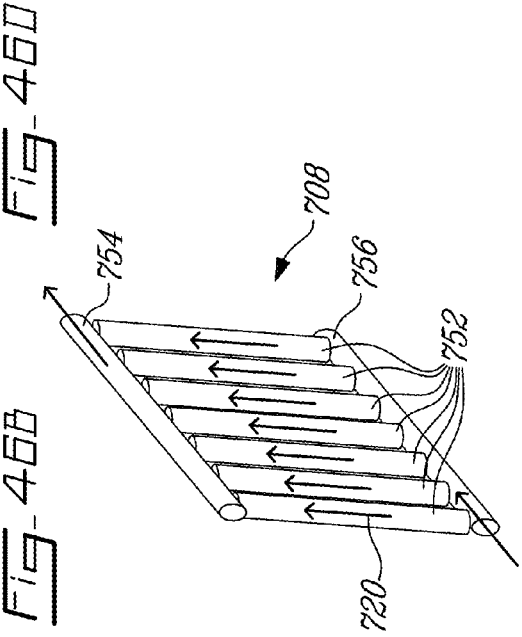
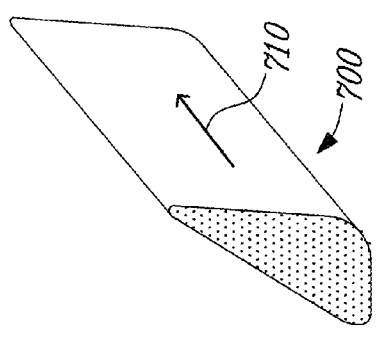
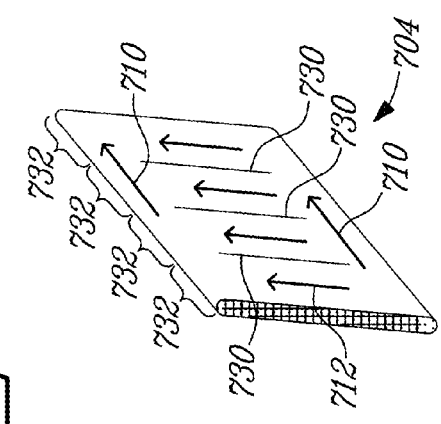

SUN TRACKING LIGHT DISTRIBUTOR SYSTEM

TECHNICAL FIELD

The invention relates to light distribution in open and closed photosynthetic culture aqueous systems which use the sun as a light source, for example for the production of algae. The light distribution walls are adapted to be oriented with a displacement system to track the sun and provide a distribution of the light in the aqueous volume.

BACKGROUND OF THE ART

Photosynthetic culture in aqueous liquids is often used for the production of algae. Two main types are known in the art, the open-ended systems such as ponds and basins and the closed systems such as photo-bioreactors (PBR). The aqueous liquid provided in the system typically includes water and the photosynthetic culture organisms such as algae or other species that use photosynthesis, such as microorganisms. Photosynthetic culture is known to require a light intensity much lower than the maximum solar light intensity. Studies have shown that optimal intensities for photosynthesis can be of the order of 10% of the maximum solar light intensity. Light distribution within an aqueous system is often referred to as "light dilution" in the field of algae culture. The higher the light dilution factor, the more significant the impact on the production of algae.

It is well known that the sun moves westward in the sky during daytime and that its maximum altitude (culmination) changes throughout the year. The sun is at its maximum altitude at solar noon each day. Solar noon occurs exactly half way between sunrise and sunset. In the northern hemisphere, the sun is due south at solar noon. The sun altitude passes from about 68° at summer solstice to about 21° at winter solstice for locations close to the 45$^{th}$ parallel of latitude. At these latitudes the maximum solar altitude at both spring and fall equinoxes is about 45°.

The prior art discusses different configurations to allow light to penetrate the aqueous liquid of the aqueous systems. These configurations either do not take into account the solar position throughout the day and throughout the year or can exhibit prohibitive optical losses or alignment precision requirements.

In prior art systems, light distributors are used in open and closed photosynthetic culture aqueous systems to capture the light from the sun and distribute it within the volume of aqueous liquid. In some systems, the light distributor includes two light distribution walls provided at an angle at a bottom end to create a V-shape or provided in a substantially parallel orientation to create a rectangular or parallelogram shape. The light distribution walls are made of a transparent material allowing sunlight to pass therethrough. An interior side of the two light distribution walls creates an elongated channel. The sunlight is received in the elongated channel and is distributed through the light distribution walls in the aqueous liquid. The light distribution walls are disposed in the photosynthetic culture such that at least part of an exterior side of the walls is in contact with the aqueous liquid.

The adjacent light distributors have a longitudinal dimension much greater than the height of their walls, thereby creating elongated channels. In use in a photosynthetic culture aqueous system, a plurality of adjacent light distribution channels are provided at the interface between the air and the aqueous liquid.

Prior art light distributor systems are static, as shown in FIG. 1. FIG. 1 shows the impact of the inclination of the sun on the light dilution in the aqueous liquid for a V-shaped light distribution channel 402 (FIG. 1A, FIG. 1C, FIG. 1E) and for a parallelogram-shaped light distribution channel 404 (FIG. 1B, FIG. 1D, FIG. 1F) in a static light distribution system 400, at three solar noon inclinations including summer (FIG. 1A, FIG. 1B), spring or fall (FIG. 1C, FIG. 1D) and winter (FIG. 1E, FIG. 1F).

A hypothetical light entry surface 412 at the top surface of the V-shaped light distribution channel receives the sun rays. The light distribution surface 414 is along the walls of the V-shaped channel or of the parallelogram channel. The horizon 418 is shown schematically.

The sun rays are illustrated schematically as entering the light distribution channels from the angle at which the sun is located. The aqueous liquid 406 is provided outside of the light distribution channel and is represented by the dotted filling surrounding the channel. The container for the aqueous liquid is omitted to simplify the drawings and the parallelogram channel therefore appears bottomless on the figure. The hatching represents the region of light dilution 408 in the aqueous liquid and varies depending on the orientation and reflection of the sunlight rays within the channel.

When the photosynthetic culture is an open-ended system, the two light distribution walls are sidewalls of a transparent structure and can be joined at the bottom to form a unitary transparent structure which is V-shaped or parallelogram-shaped. A transparent top surface can be provided to close the structure.

For closed systems, such as a PBR, elongated conduits are shaped and juxtaposed to create a light distribution channel or region between the rows of conduits. The elongated conduits are made of a thin transparent material and the aqueous algae culture occurs within the conduits. The elongated conduits can be provided with substantially flat sides. The sides of the adjacent elongated conduits therefore act as the light distribution walls and the solar rays are able to be distributed within the conduits. The conduits may be drop-shaped or rectangular depending on the application.

There is a need to improve light distribution in open-ended and closed aqueous systems to benefit from exposure to as much light as possible from the sun.

SUMMARY

In one broad aspect of the present invention, there is provided a sun-tracking light distributor system for use in one of an open-ended system and a closed photo-bioreactor for a photosynthetic culture having an aqueous liquid. The system comprises: two light distribution walls made of a transparent material allowing sunlight to pass therethrough, the two light distribution walls creating an elongated channel with an interior space adapted to receive the sunlight and an exterior surface adapted to be partly immersed in the aqueous liquid in use; and a displacement system operatively connected to at least one of the two light distribution walls, the displacement system being adapted to change an orientation of the at least one of the two light distribution walls to track a solar position with respect to at least one axis.

In one embodiment, the photosynthetic culture is in a closed photo-bioreactor, the light distribution walls are facing sidewalls of adjacent sections of transparent tube, the tube being adapted to contain the aqueous liquid, the interior space of the channel being provided by a spacing between the adjacent sections of tube.

In one embodiment, the tube has one of a drop-shaped cross-section and an inverted V-shaped cross-section.

In one embodiment, the tube has one of a parallelogram cross-section and an obround-shaped cross-section.

In one embodiment, the tube is separated in upright sections, the upright sections defining a path for circulation of the aqueous liquid in the tube.

In one embodiment, each of the light distribution walls is formed by neighboring upright tubes disposed side-by-side along the elongated channel, the neighboring upright tubes being one of independent and solidary.

In one embodiment, the two light distribution walls are oriented to be provided at an angle at a bottom end thereby creating an elongated V-shaped channel, said elongated V-shaped channel being one of closed and open at said bottom end.

In one embodiment, the V-shaped channel is open at said bottom end and has a bottom wall extending between bottom ends of the light distributions walls.

In one embodiment, the two light distribution walls are oriented to create a parallelogram-shaped channel.

In one embodiment, the displacement system includes attachment means connected to the tubes to give at least one of an inclination, a shape, a rigidity and a support to at least one of the sidewalls.

In one embodiment, the tubes are made of a flexible material and a shape of the light distribution walls is variable.

In one embodiment, the photosynthetic culture is an open-ended system, the two light distribution walls are sidewalls of a transparent structure, the transparent structure being adapted to be partly immersed in the aqueous liquid in use.

In one embodiment, the transparent structure is an open-ended parallelogram-shaped transparent structure.

In one embodiment, the transparent structure is an open-ended V-shaped transparent structure.

In one embodiment, the transparent structure has a transparent top surface.

In one embodiment, the transparent top surface bears a light concentrating element.

In one embodiment, the transparent structure is at least partly hollow.

In one embodiment, the transparent structure has at least one channel formed therein to circulate at least one of air, water, gas, nutrients.

In one embodiment, a shape of the light distributor walls includes at least one of a curved section and an angled section.

In one embodiment, a longitudinal axis of the elongated channel is provided in an East-West orientation.

In one embodiment, the displacement system is adapted to change an inclination of both of the two light distribution walls of the elongated channel with a single displacement operation.

In another broad aspect of the present invention, there is provided a method for distributing light in one of an open-ended photo-bioreactor and a closed photo-bioreactor for a photosynthetic culture. The method comprises providing a sun-tracking light distributor system in the one of an open-ended photo-bioreactor and a closed photo-bioreactor; and changing an orientation of at least one of the light distribution walls using the displacement system to allow tracking of the sun.

In the present specification, the term "transparent" is intended to mean a material which allows sunlight of the wavelength band of interest to pass therethrough with limited absorption in the material itself. For the production of algae, an example wavelength band of interest can be visible light in the range of 400 nm-700 nm.

BRIEF DESCRIPTION OF THE DRAWINGS

Having thus generally described the nature of the invention, reference will now be made to the accompanying drawings, showing by way of illustration example embodiments thereof and in which:

FIG. 1 (Prior Art) includes FIG. 1A, FIG. 1B, FIG. 1C, FIG. 1D, FIG. 1E and FIG. 1F which show the impact of the inclination of the sun on the light dilution in the aqueous liquid for a V-shaped light distribution channel (FIG. 1A, FIG. 1C, FIG. 1E) and for a parallelogram-shaped light distribution channel (FIG. 1B, FIG. 1D, FIG. 1F) in a light distribution system which does not follow the position of the sun, at three solar noon inclinations including summer (FIG. 1A, FIG. 1B), spring or fall (FIG. 1C, FIG. 1D) and winter (FIG. 1E, FIG. 1F);

FIG. 2 includes FIG. 2A and FIG. 2B in which

FIG. 4 includes FIG. 4A to 4C in which

FIG. 5 includes FIG. 5A and FIG. 5B in which

FIG. 6 includes FIG. 6A and FIG. 6B in which

FIG. 7 includes FIG. 7A and FIG. 7B in which

FIG. 9 includes FIG. 9A and FIG. 9B in which

FIG. 12 includes FIG. 12A and FIG. 12B in which FIG. 12A shows the penetration of light in a basin without light distributors and FIG. 12B with V-shaped light distributors;

FIG. 13 includes FIG. 13A and FIG. 13B in which FIG. 13A shows and an example displacement system which orients the light distributors using a handle for Summer and FIG. 13B for Fall;

FIG. 18 includes FIG. 18A and FIG. 18B in which

FIG. 19 includes FIG. 19A and FIG. 19B in which

FIG. 35 shows an example V-shaped structure with an internal triangular structure;

FIG. 38 includes FIG. 38A, FIG. 38B and FIG. 38C which show the constant light dilution in the aqueous liquid for a V-shaped light distribution channel in a light distribution system which is adapted for sun-tracking, even if the inclination of the sun changes, at three solar noon inclinations including summer (FIG. 38A), spring or fall (FIG. 38B) and winter (FIG. 38C);

FIG. 39 includes FIG. 39A and FIG. 39B which show the constant light dilution in the aqueous liquid for a convex V-shaped variant of the V-shaped light distribution channel of a light distribution system which is adapted for sun-tracking, even if the inclination of the sun changes, at two solar noon inclinations including summer (FIG. 39A) and spring or fall (FIG. 39B);

FIG. 40 includes FIG. 40A and FIG. 40B which show the constant light dilution in the aqueous liquid for a concave V-shaped variant of the V-shaped light distribution channel of a light distribution system which is adapted for sun-tracking, even if the inclination of the sun changes, at two solar noon inclinations including summer (FIG. 40A) and spring or fall (FIG. 40B);

FIG. 43 includes FIG. 43A and FIG. 43B which show the constant light dilution in the aqueous liquid for a parallelogram-shaped light distribution channel in a light distribution system which is adapted for sun-tracking, even if the inclination of the sun changes, at two solar noon inclinations including summer (FIG. 43A) and spring or fall (FIG. 43B);

FIG. 44 includes FIG. 44A and FIG. 44B which show the constant light dilution in the aqueous liquid for a light distribution system having displaceable light distribution walls adapted for sun-tracking and forming a parallelogram light distribution channel, even if the inclination of the sun changes, at two solar noon inclinations including summer (FIG. 44A) and spring or fall (FIG. 44B);

FIG. 45 includes FIG. 45A and FIG. 45B which show an embodiment for the shape of the container for the aqueous liquid outside of the parallelogram-shaped light distribution channel including independent adjacent conduits, each conduit forming a single wall, the aqueous liquid traveling in the conduits, the conduit walls being oriented to be separated by parallelogram light distribution channels, at two solar noon inclinations including summer (FIG. 45A) and spring or fall (FIG. 45B);

FIG. 46 includes FIG. 46A, FIG. 46B, FIG. 46C, FIG. 46D and FIG. 46E which show variants for the longitudinal displacement of the aqueous liquid in the elongated conduit walls, including a longitudinal displacement in a drop-shaped cross-section conduit (FIG. 46A), a longitudinal displacement in a straight wall (FIG. 46B) which is shown to be obround-shaped, a longitudinal displacement combined with an upward displacement in a straight wall separated in sections in the longitudinal direction (FIG. 46C), a longitudinal displacement created by a upward and downward displacement in a straight wall in which a path is predefined (FIG. 46D), a vertical displacement in independent sections of the conduit (FIG. 46E);

It will be noted that throughout the appended drawings, like features are identified by like reference numerals.

DETAILED DESCRIPTION

A sun-tracking light distribution system can be provided to allow efficient light distribution in open and closed photosynthetic culture aqueous systems which use the sun as a light source. The sun-tracking light distribution system has a light distribution channel and a displacement system. The light entry surface of the light distribution channel is to be oriented so as to capture a significant portion of the light from the sun and the light distribution surface distributes it within the volume of aqueous liquid, regardless of the time of day or day of year. At least one of the light distribution wall of the channels will be adapted to be inclined as a function of the maximum solar altitude to change the orientation of the light entry surface.

V-shaped light distribution channels and parallelogram-shaped light distribution channels are presented herein. V-shaped and rectangular-shaped transparent structures to be inserted in open-ended photosynthetic culture aqueous systems are described. Elongated rows of conduits which form V-shaped and rectangular-shaped light distribution channels are also described for use in closed photosynthetic culture aqueous systems.

FIG. 38 shows the light dilution in the aqueous liquid for an example embodiment of a V-shaped light distribution channel 502 in a light distribution system 500 which is adapted for sun-tracking. The angle of the light entry surface 512 with respect to the horizon 418 is made to change by the displacement system (not shown in the figure) of the light distribution system 500 to track a general inclination of the sun. The light dilution stays substantially constant even if the inclination of the sun changes.

FIG. 39 and FIG. 40 show the light dilution for two variants of the V-shaped light distribution channel of a light distribution system which is adapted for sun-tracking FIGS. 39A and 39B show a convex V-shape and FIGS. 40A and 40B show a concave V-shape. As will be readily understood, various other shapes can be used for the shape of the channel such as a parabolic shape, a U-shape, etc.

Figure 41C:
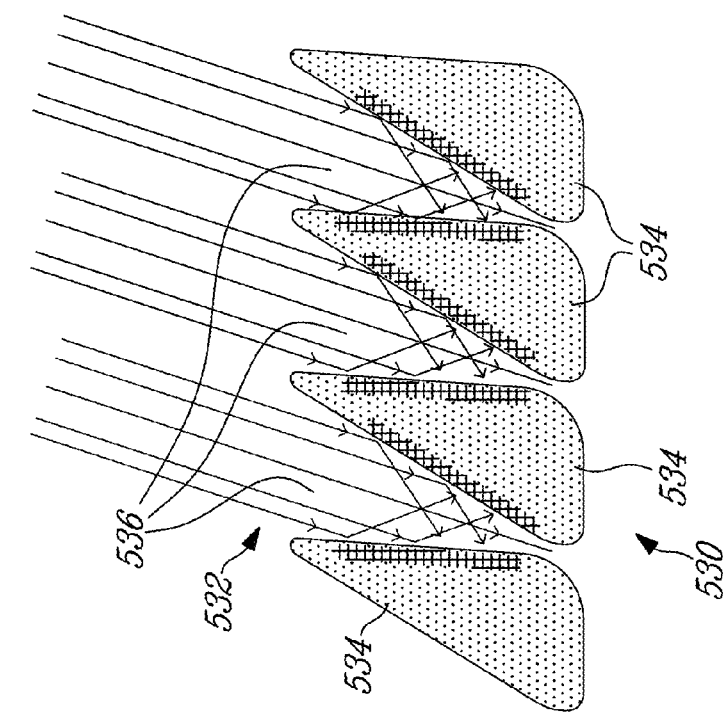
FIG. 41 includes FIG. 41A, FIG. 41B and FIG. 41C which show variants for the shape of the container for the aqueous liquid outside of the V-shaped light distribution channel (FIG. 41A), including a basin (FIG. 41B) which receives the V-shaped light distributor system forming a plurality of V-shaped distribution channels and elongated tubes (FIG. 41C) in which the aqueous liquid travels, separated by V-shaped light distribution channels.
Figure 41B:
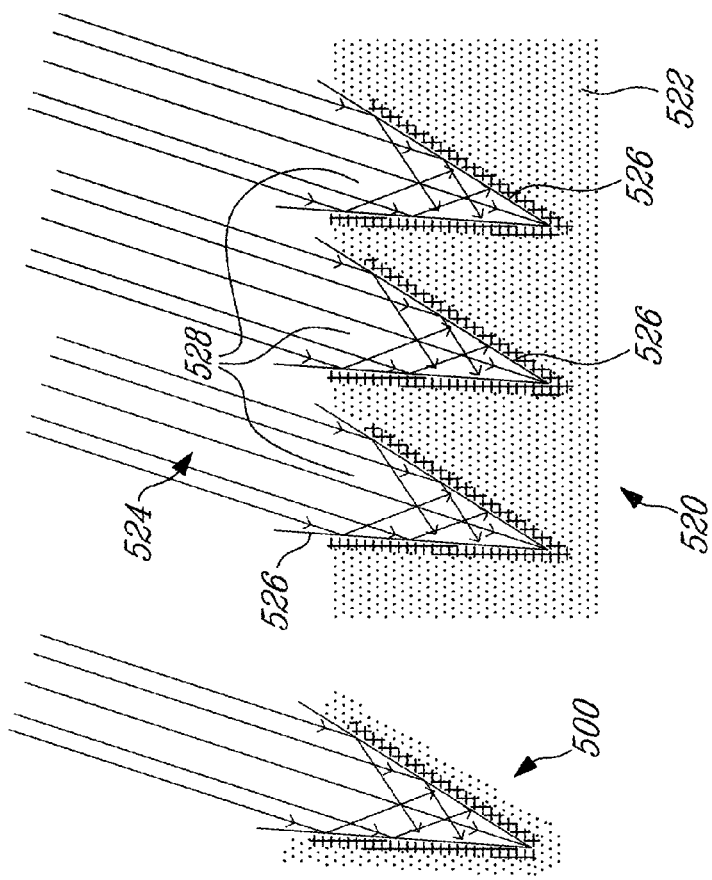
Figure 41A:
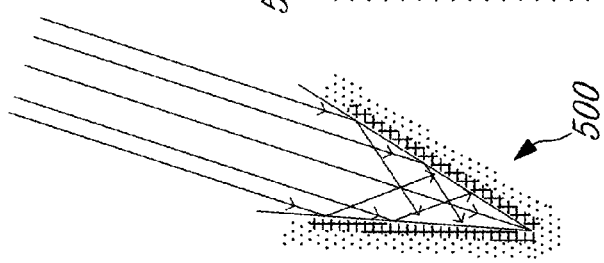

FIG. 41 shows variants for the shape of the container for the aqueous liquid outside of the V-shaped light distribution channel (FIG. 41A). In the culture system 520 of FIG. 41B, a basin 522 receives the V-shaped light distributor system 524 which includes a plurality of V-shaped structures 526. The interior of the V-shaped structures form a plurality of V-shaped distribution channels 528. In the culture system 530 of FIG. 41C, the light distribution system 532 includes elongated tubes or conduits 534 in which the aqueous liquid travels. The conduits 534 are separated by V-shaped light distribution channels 536.

Figure 42B:
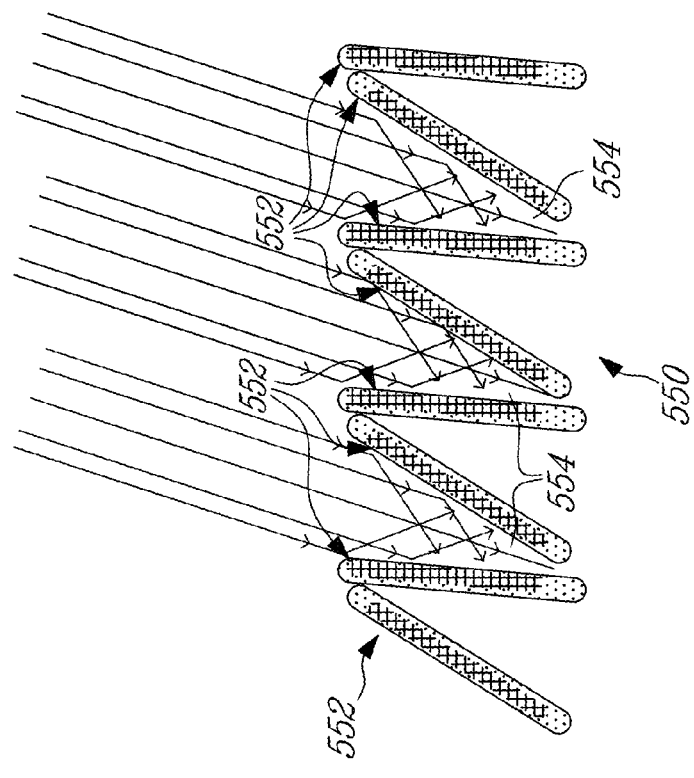
FIG. 42 includes FIG. 42A and FIG. 42B which show other variants for the shape of the container for the aqueous liquid outside of the V-shaped light distribution channel (FIG. 41A), including inverted-V adjacent conduits, each conduit forming two walls joined at an upper end (FIG. 42A) and independent adjacent conduits, each conduit forming a single wall (FIG. 42B), the aqueous liquid traveling in the conduits, the conduit walls being oriented to be separated by V-shaped light distribution channels.
Figure 42A:
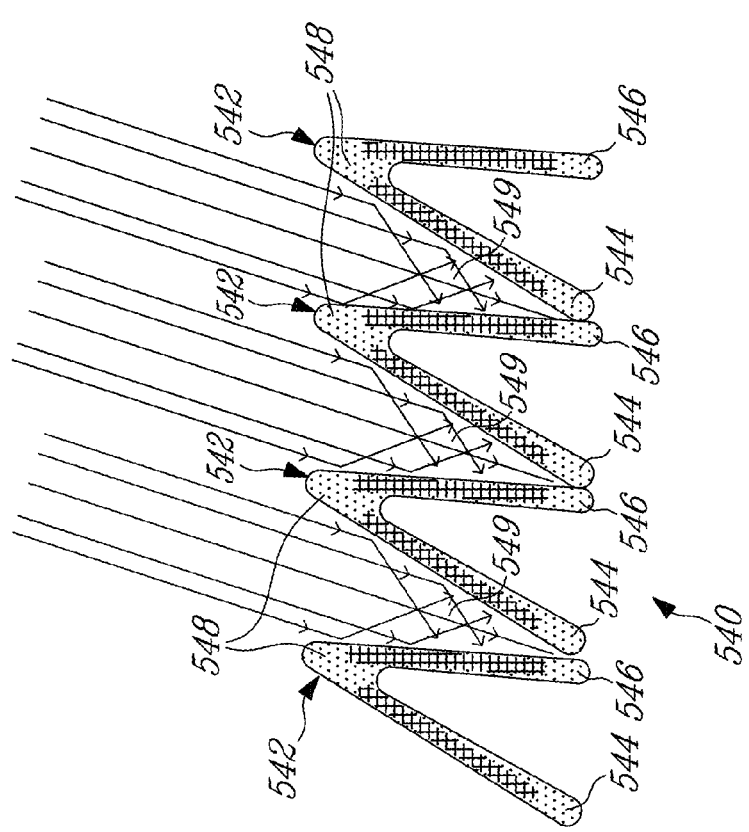

FIG. 42 shows other variants for the shape of the container for the aqueous liquid outside of the V-shaped light distribution channel. In the light distribution system 540 of FIG. 42A, the conduits are inverted-V conduits 542, each conduit forming two walls 544, 546 joined at an upper end 548. Adjacent walls of the inverted-V conduits 542 form the V-shaped light distribution channels 549. In the light distribution system 550 of FIG. 42B, the conduits are independent adjacent conduits 552, each conduit forming a single wall. The aqueous liquid travels in the conduits 552, the conduits 552 are oriented to be separated by V-shaped light distribution channels 554.

In the culture system of FIG. 43, a basin (not shown) receives the light distributor system 600 which includes a plurality of rectangular-shaped structures 602. The interior of the rectangular-shaped structures forms a plurality of rectangular-shaped distribution channels 604. FIG. 43 shows the constant light dilution in the aqueous liquid for a rectangular-shaped light distribution channel in a light distribution system which is adapted for sun-tracking.

FIG. 44 shows the constant light dilution in the aqueous liquid for a light distribution system having displaceable light distribution walls adapted for sun-tracking and forming a parallelogram light distribution channel, even if the inclination of the sun changes, at two solar noon inclinations including summer (FIG. 44A) and spring or fall (FIG. 44B). FIG. 44 shows a light distribution system 620 having displaceable light distribution walls 628 adapted for sun-tracking and forming a parallelogram light distribution channel 624 whose light distribution walls 628, which are affixed to the bottom surface, can be rotated or displaced. The bottom surface 630 can be the ground. In order to yield improved results, a reflective bottom surface may be used. Diffuse reflection may be sufficient.

When the walls are inclined (FIG. 44A), a parallelogram-shaped light distribution channel is formed. When the walls are upright (FIG. 44B), a rectangular light distribution channel, such as the one provided by the rectangular-shaped structures of FIG. 43, is created. If the walls are upright at solar noon during the summer at latitudes close to the equator, as shown in FIG. 1B, the light dilution is very poor. However, when the walls are upright at solar noon during the spring or fall at the equator or at other times of the day in northern or southern latitudes, as shown in FIG. 44B, the light dilution is greater. In order to achieve an interesting light dilution throughout the day in spring, summer and fall in a plurality of latitudes, the walls can be inclined as shown in FIG. 44A. A displacement system (not shown in the figure) provides the proper inclination for the light distribution walls 628.

FIG. 45 shows a light distribution system 650 in which the container for the aqueous liquid is an elongated obround conduit 652. This conduit 652 can be a single conduit which is folded at the longitudinal ends of the parallelogram-shaped light distribution channel to create a snaking arrangement (see FIG. 4C for a snaking arrangement creating a V-shaped light distribution channel) or can be a plurality of elongated conduits which are disposed side-by-side to create the light distribution channels. The parallelogram light distribution channel 654 is formed by facing walls of adjacent conduit sections. In this embodiment, the bottom surface 656 of the parallelogram light distribution channel can be reflective for improved light dilution purposes or it can simply be the ground.

In an example embodiment, the elongated parallelogram-shaped channel may have a height of 1 m and a width of 0.3 m. Its length, along the longitudinal dimension of the channel which is perpendicular to the plan of FIG. 45, may be 2 m. In order to create such a channel, elongated obround tubular conduits measuring 1 m in height by 2 m in length are used and installed in a substantially parallel arrangement, 0.3 m apart. Each elongated obround tubular conduit is subdivided in vertical tubes of about 0.1 m in width along the longitudinal dimension of the channel, their height being the height of the conduit, using section separators which can prevent or allow circulation of the aqueous liquid between the vertical tubes. The thickness of the conduits in this example embodiment is 0.1 m. As will be readily understood, the characteristics of the supporting structure will dictate the dimensions of the conduits. For example, in other embodiments, conduit lengths much longer than 2 m may be used.

FIG. 46 shows variants for the longitudinal displacement of the aqueous liquid in the elongated conduits. In FIG. 46A, the aqueous liquid travels in the longitudinal direction 710 in a drop-shaped cross-section conduit 700. In FIG. 46B, the aqueous liquid travels in the longitudinal direction 710 in a obround shaped conduit 702. In FIG. 46C, the obround shaped conduit 704 includes open-ended transversal section separators 730. The aqueous liquid therefore travels along the longitudinal direction 710 and with a upward displacement 712 in the sections 732. In FIG. 46D, the obround shaped conduit 706 includes transversal separators 740, 742 defining a path for aqueous liquid flow. The aqueous liquid therefore travels in the longitudinal direction but along a path which includes upward 712, U-turn 714, 716 and downward 718 displacements. In FIG. 46E, independent vertical (transversal or upright) sections 752 are provided in the elongated conduit 708. The aqueous liquid travels in the longitudinal direction in manifolds 754 and 756 and upwards within the independent sections 752.

As will be readily understood, the obround cross-section for the conduit is used for ease of representation of the conduits. The shape of the cross-section of the conduit, the pressure within the conduit and the attachment to the displacement system will affect the shape of the cross-section of the conduit in use.

The displacement system allows proper positioning of the light distribution walls with respect to the sun, depending on its current position in the sky. This displacement system can be individual for each light distribution wall or can be a global displacement system which controls a plurality of light distribution walls or all of them. The displacement system displaces the light distribution walls along at least one axis.

Figure 47A:
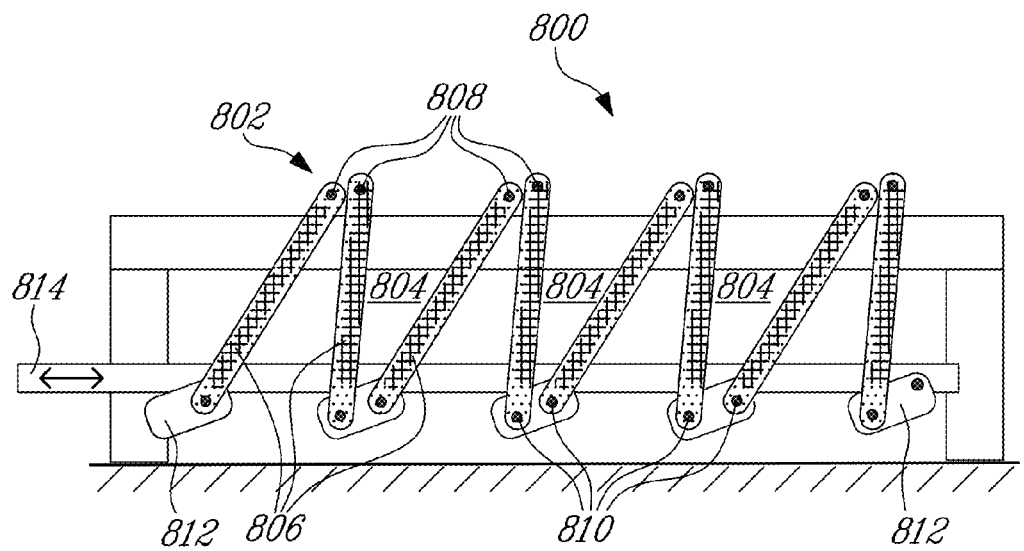
FIG. 47 includes FIG. 47A and FIG. 47B which show an example displacement system to change the orientation of the walls in a light distribution system with V-shaped light distribution channels, for two different orientations.
Figure 47B:
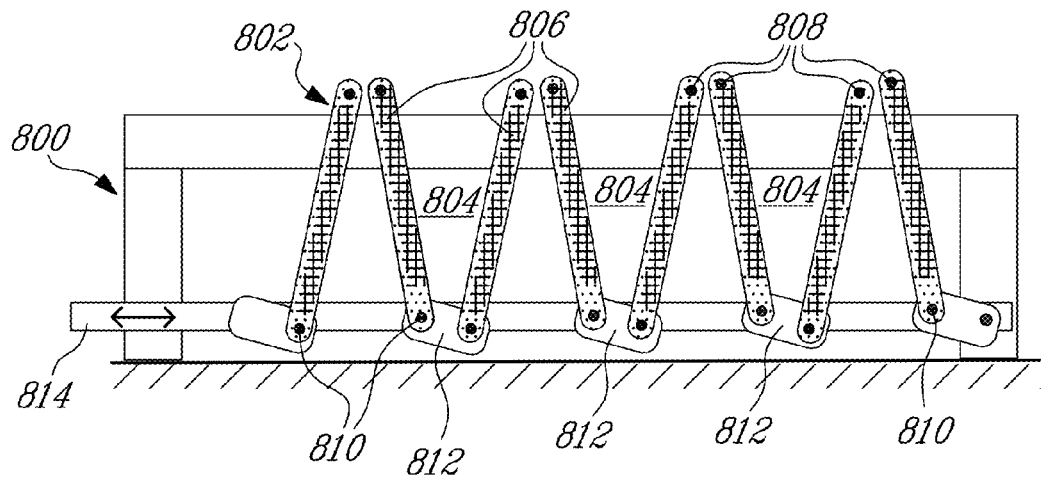

FIG. 47 shows an example displacement system 800 to change the orientation of the walls in a light distribution system 802 with V-shaped light distribution channels 804. The conduits 806 are affixed to fixed elongated rods 808 at their top end. The bottom ends 810 of the conduits are affixed to plates 812. The bottom ends 810 of two adjacent conduits 806 are affixed to a same plate 812. The conduits form V-shaped channels 804. The plates 812 are affixed to a transversal handle 814. The movement of the transversal handle 814 between two end positions causes the plates 812 to pivot, thereby changing the orientation of the light distribution walls 806. The movement of the handle 814 can be controlled by an actuator. As will be readily understood, the top ends of the conduits can also be provided on plates adapted to pivot in another embodiment.

Figure 48A:
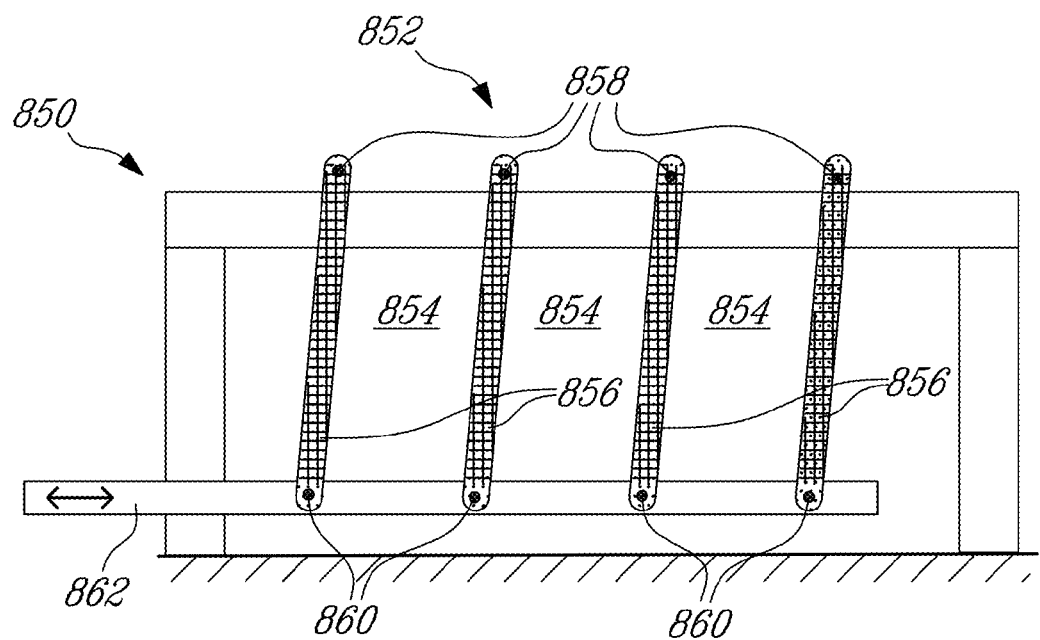
FIG. 48 includes FIG. 48A and FIG. 48B which show an example displacement system to change the orientation of the walls in a light distribution system with parallelogram-shaped light distribution channels, for two different orientations.
Figure 48B:
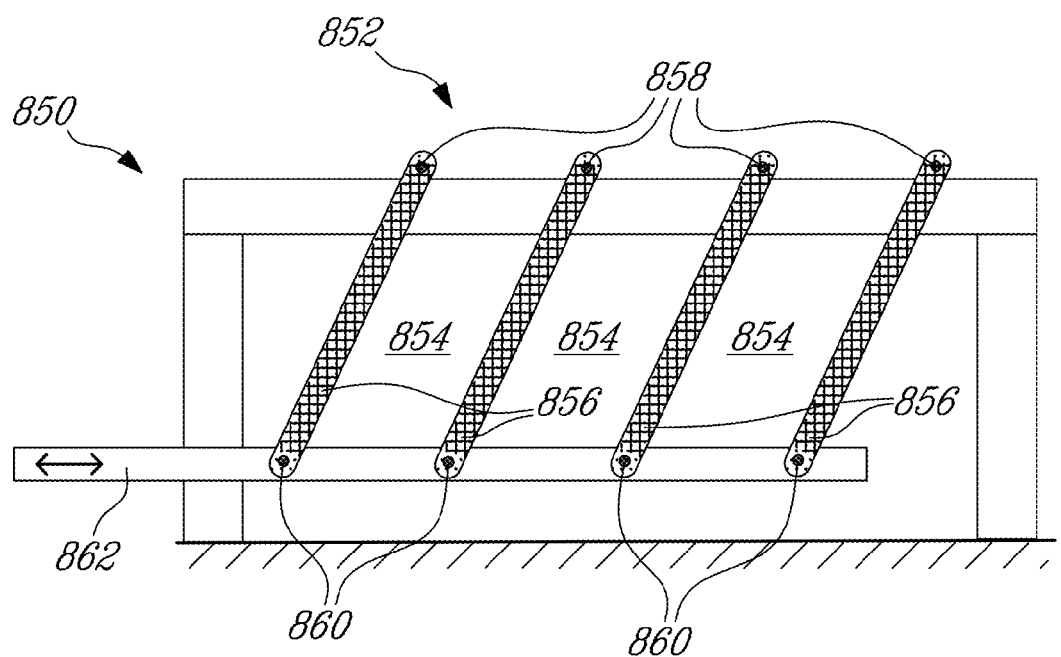

FIG. 48 shows an example displacement system 850 to change the orientation of the walls in a light distribution system 852 with parallelogram-shaped light distribution channels 854. The conduits 856 are affixed to fixed elongated rods 858 at their top end. The bottom ends 860 of the conduits are affixed to a transversal handle 862. The conduits form parallelogram-shaped channels 854. Movement of the transversal handle 862 between two end positions causes the conduits 856 to pivot.

In use, the longitudinal axis of the light distribution channels can be oriented along the East-West direction. Alternatively, the longitudinal axis of the elongated channel can be disposed in a North-South orientation. The displacement system will typically need to adjust the inclination of the light distribution wall(s) less frequently if the longitudinal axis of the elongated channel is in the East-West direction instead of the North-South direction. As will be readily understood, one can choose to dispose the longitudinal axis of the elongated channels in an orientation other than North-South or East-West and still adjust the inclination of at least one of the two light distribution walls using the displacement system in response to the sun's altitude throughout the day and the year.

When the channels are provided along the East-West orientation, the inclination of the channel surfaces can be calculated and positioned using the maximum altitude of the sun in a given day. For the rest of the day, the sun rays will be sufficiently well oriented to still be captured within the light distributors and distributed within the volume. In most situations, the orientation of the channel surfaces will therefore not need to be changed during the day and can only be modified once a day or even once every few days, in order to maintain an efficient light dilution factor. As will be readily understood, should one wish to adjust the orientation more often, it will be directly possible to do so. Any frequency of adjustment of the inclination of the channel surfaces may be used. As will be readily understood, the tracking may be approximate, within a precision range acceptable for the application.

Referring back to FIG. 2 to FIG. 37, embodiments which create a V-shaped elongated channel will be described in more detail. As will be readily understood, features described in relation with the embodiments which have a V-shaped light distribution channel may also be optionally provided in embodiments which have a parallelogram-shaped light distribution channel, and vice-versa.

When the photosynthetic culture is an open-ended system, the two light distribution walls are sidewalls of a V-shaped transparent structure and the two light distribution walls provided at an angle and oriented to converge at the bottom end are joined to form a unitary V-shaped transparent structure. A transparent top surface can be provided to close the V-shaped structure into an inverted-triangle structure. If the light distribution walls do not meet at their bottom end, a bottom surface may be provided between the bottom ends of the light distribution walls to create a V-shaped channel with an enlarged bottom end, similar to a U-shaped channel.

Figure 2A:
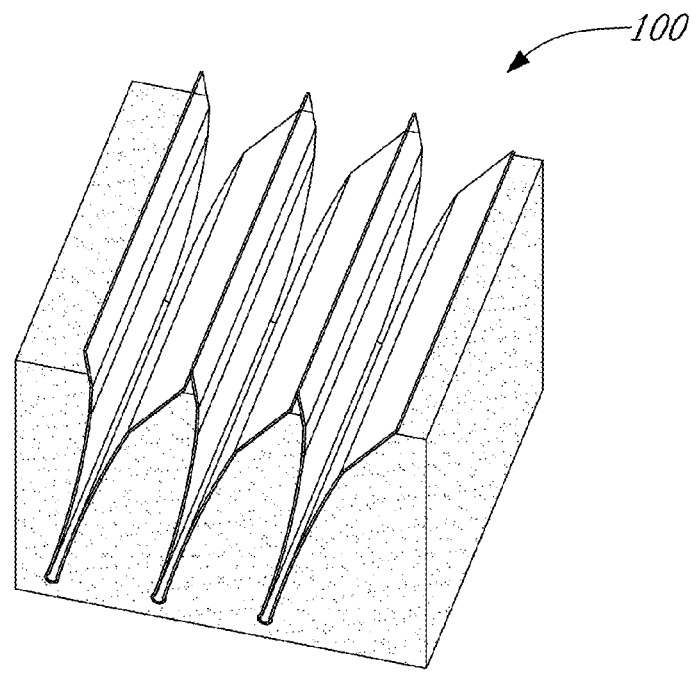
FIG. 2A shows open-ended transparent V-shaped structures in perspective in an open-ended basin or pond and FIG. 2B shows a side view of the open-ended transparent V-shaped structures of FIG. 2A.
Figure 2B:
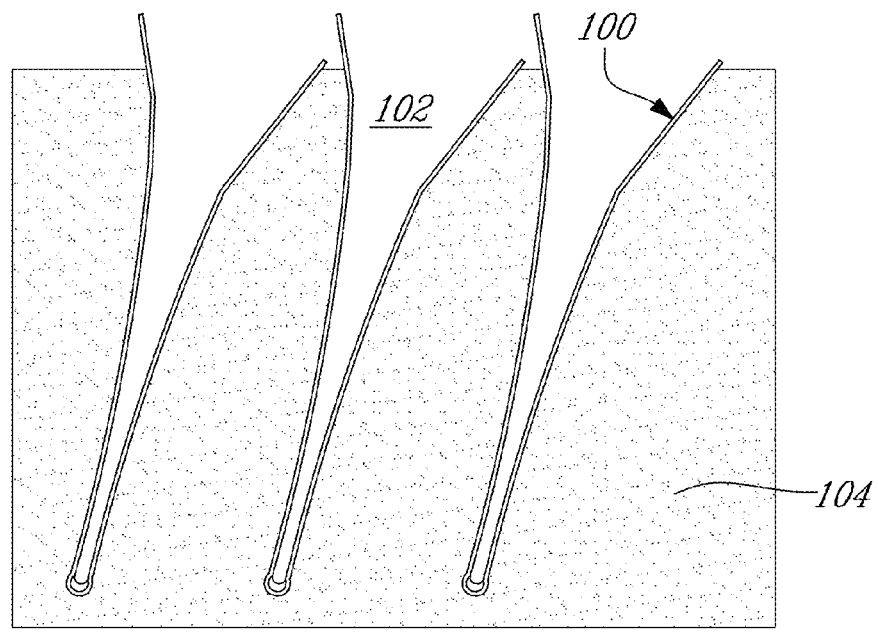
Figure 3:
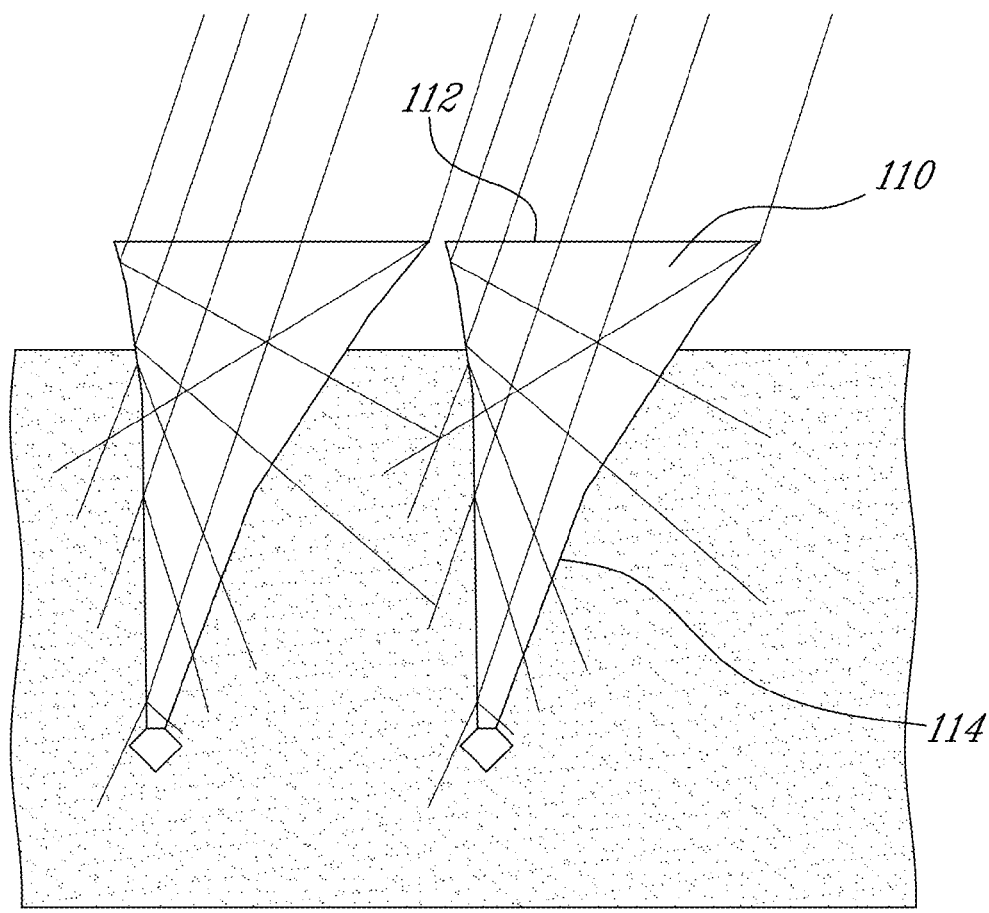
FIG. 3 shows closed transparent V-shaped structures in an open-ended basin or pond with the reflections of the light rays being apparent.

With reference to FIG. 2A and FIG. 2B, these transparent V-shaped structures can be open-ended 100. With reference to FIG. 3, these transparent V-shaped structures can be closed structures 110, with a substantially triangular shape, the triangle being inverted with its base at the top. The triangular V-shaped structures can be hollow and/or have channels formed therein.

Figure 5A:
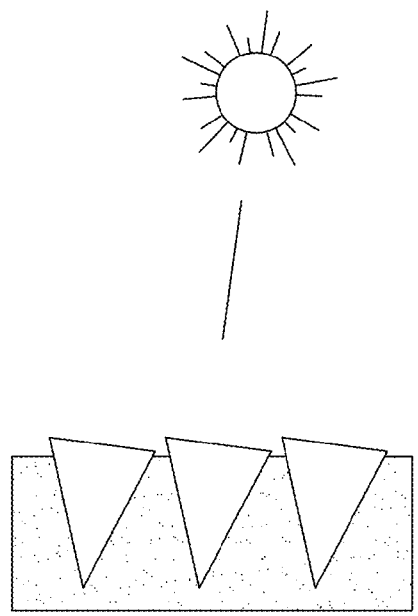
FIG. 5A and FIG. 5B show an example orientation of the V-shaped structures in an open-ended system for the summer months and the fall months, respectively, in a moderate climate region.
Figure 5B:
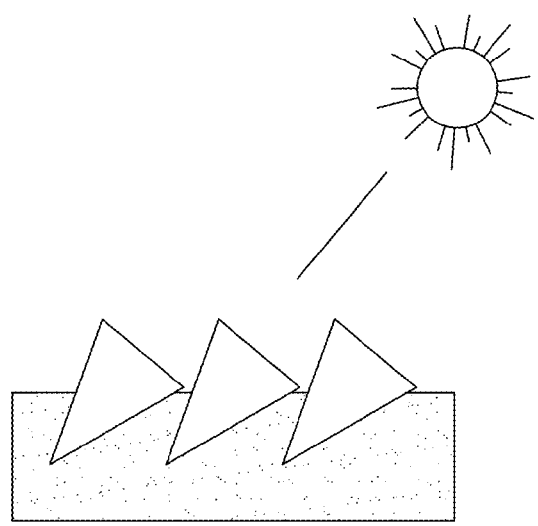

FIG. 5A and FIG. 5B show an example orientation of the V-shaped structures in an open-ended system for the summer months and the spring/fall months, respectively, in a moderate climate region. The longitudinal axis of the elongated V-shaped surfaces are oriented in the East-West direction, the sun-tracking is performed along a single axis.

The V-shaped structures are rigid and create elongated V-shaped channels 102 in the basin. These V-shaped channels 102 are filled with air. The rigid material is transparent and can be made of plastic, glass or any other transparent material. It is, for example, made of PMMA, polycarbonate or even glass. It can be made of extruded plastic material. It can sustain the pressure from the aqueous liquid of the basin 104. The elongated channels 102 form chambers which capture and trap the solar rays. Unfortunately, dirt, water and other contaminants can accumulate in the channels. As will be readily understood, the open-ended region of the V-shaped structures is to be provided above the surface level of the aqueous liquid in the basin.

The open-ended region of the V-shaped structure can be covered with a transparent film (not shown) which can be affixed permanently or temporarily, for example by adhesion, to the top of the exterior surfaces of the V-shaped structure. This transparent film can prevent algae, dirt and aqueous liquid from entering the open-ended V-shaped structure. This transparent film can be replaced periodically.

An example open-ended V-shaped light distributor has a shape similar to that shown in FIG. 2B. In this example embodiment, the open-ended light entry surface has a transverse width of 10-20 cm. The light distribution wall has a height of about 30-50 cm. The length of the light distribution walls will depend on the rigidity of the materials used and of the structure created.

Referring now to FIG. 3, the triangular structures can be hollow. The triangular structure can be filled partly or fully with dry air, ethanol, glycerol, water or can be a prism of transparent material. A liquid or solid material can be inserted therein to facilitate light propagation.

The top surface of the inverted-triangle structure, namely the light-entry surface 112, will reflect some of the solar illumination towards the sky. This will result in losses. With a hollow triangle made of glass or PMMA filled with air, there will be a loss of about 8% at noon and about 15% of the total collected energy in a day. With a transparent material, for example water, which can be used within a prism cavity in the top section of the triangle, the losses will be reduced.

An example closed V-shaped light distributor has a shape similar to that shown in FIG. 3. The light entry surface 112 has a transverse width of 10-20 cm. The light distribution wall 114 has a height of about 30-50 cm. The length of the light distribution wall will depend on the rigidity of the materials used and of the structure created.

The light entry surface 112 is provided above a surface of the aqueous liquid and the light distribution walls 114 are provided partly underneath the surface of the aqueous liquid.

The light entry surface 112 can be provided with a polymer material with a low refractive index to lower the reflection losses.

A removable transparent film can be applied on the exterior surfaces of the V-shaped structure. This transparent film can help in keeping the wall intact and may prevent scratches from being formed in the wall. Algae will accumulate on the film. The film can be removed and replaced when necessary.

Figure 6A:
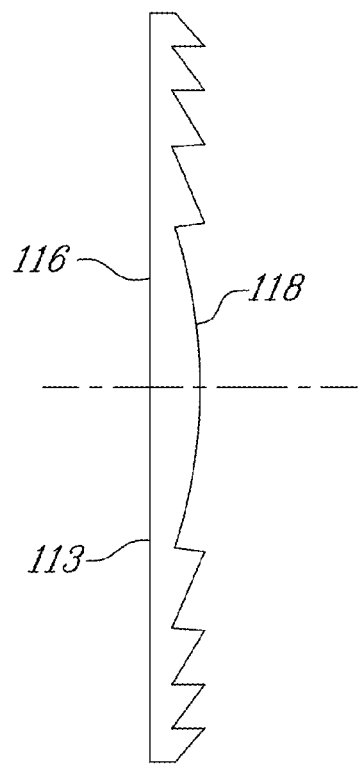
FIG. 6A shows an example Fresnel lens and FIG. 6B shows the example Fresnel lens at the light entry surface of a closed V-shaped light distributor.
Figure 6B:
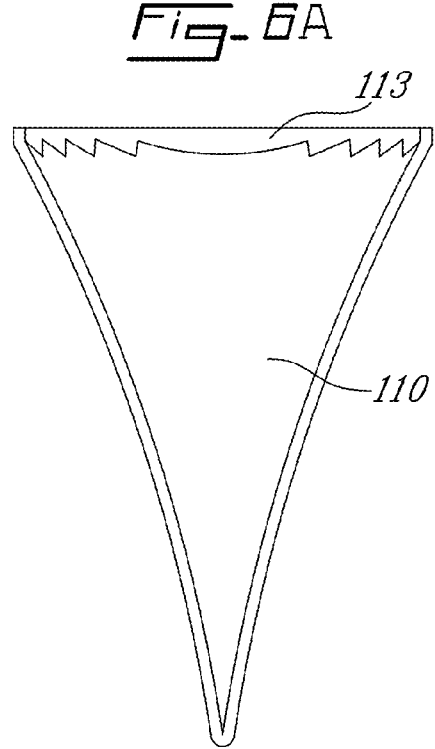

The light entry surface 112 can bear a light concentrator element 113 which allows propagating light through a channel which has a cross-section smaller than the light entry surface. A Fresnel lens is an example of such an optical component. Other example light concentrator elements include a standard converging lens of suitable focal length, a mirror (metallic or dielectric) disposed on the side of the light distribution wall, etc. An example cylindrical Fresnel lens is shown in FIG. 6A. One of its surfaces is flat 116 while the other is ridged 118. The design of the Fresnel lens allows the fabrication of a lens of large aperture and short focal length, while requiring less material than a conventional lens of similar characteristics. It can therefore be used to redirect the solar rays within the channel. FIG. 6B shows a closed V-shaped light distributor 110 with a Fresnel lens 113.

To facilitate cleaning, the flat surface 116 of the Fresnel lens may be set external to the light distributor and the ridged surface 118 may be towards the interior of the light distributor to concentrate the solar rays towards the interior of the light distributor. According to a variant, the flat surface may be towards the interior of the light distributor and the ridged surface towards the exterior of the light distributor.

Figure 7A:
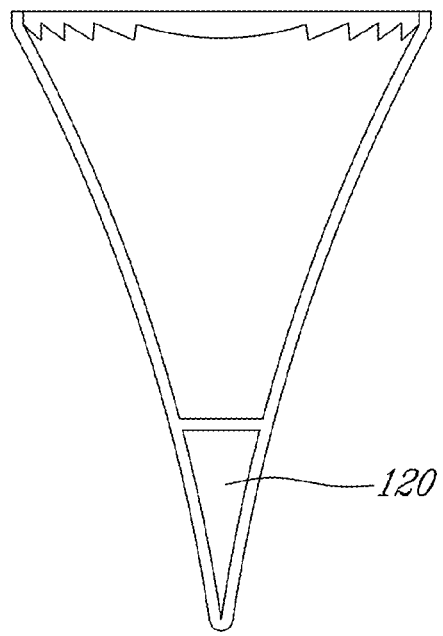
FIG. 7A shows a hollowed triangular structure manufactured to include a water chamber and FIG. 7B shows a hollowed triangular structure with a plurality of chambers or cavities formed therein.
Figure 7B:
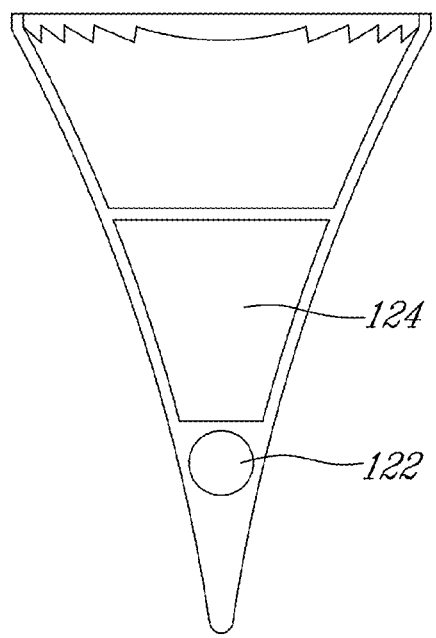
Figure 8:
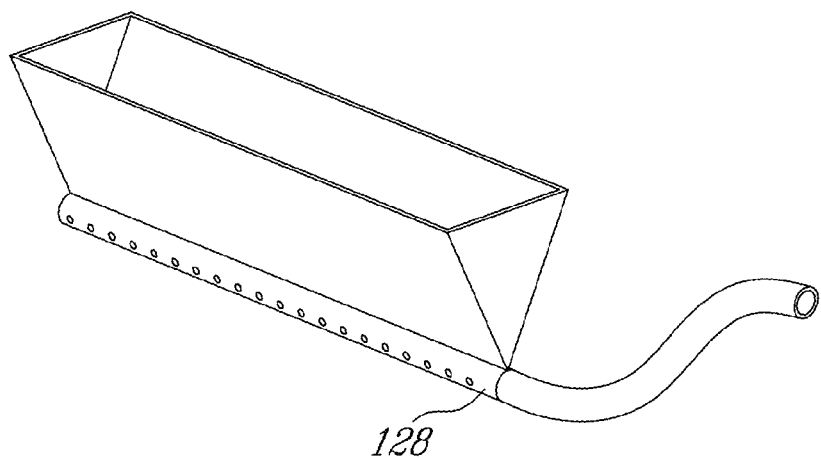
FIG. 8 shows a V-shaped structure with a perforated channel for transport and distribution of gas.

As shown in FIGS. 7A and 7B, the hollowed triangular structure can be manufactured to include a water chamber 120, 122 to assist, for example, in sinking of the V-shaped structure. A channel 124 for a transparent liquid, for example water with facultative additives can also be provided. As shown in FIG. 8, it can also be manufactured to include a perforated channel 128 for transport and distribution of air, $CO_2$ and/or gas within the aqueous system.

Figure 9A:
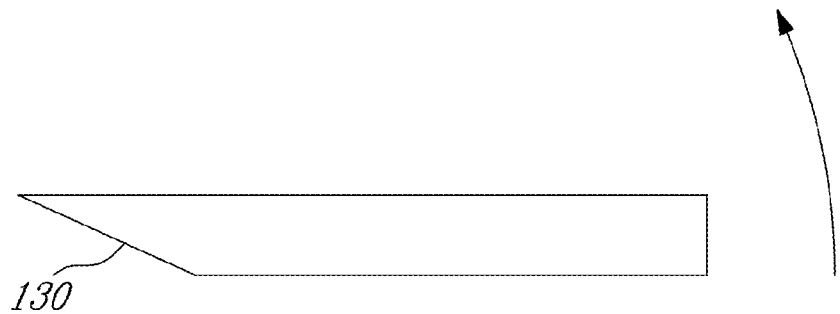
FIGS. 9A and 9B show an embodiment of the V-shaped structure with an inclined end wall, the V-shaped structure adapted to be lifted at the opposite end to allow disposal of waste and water at the inclined wall.
Figure 9B:
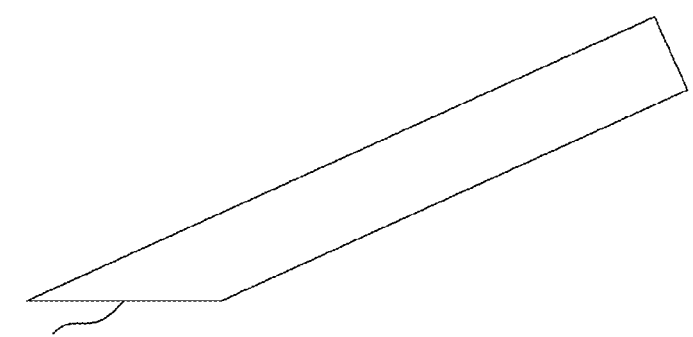

As shown in FIGS. 9A and 9B, one longitudinal end of the open-ended elongated V-shaped structure can have an inclined end wall 130 and the open-ended V-shaped structure can be adapted to be lifted at the opposite end to allow disposal of waste and water at the inclined end wall. This can be useful for cleaning purposes, for example.

Figure 10:
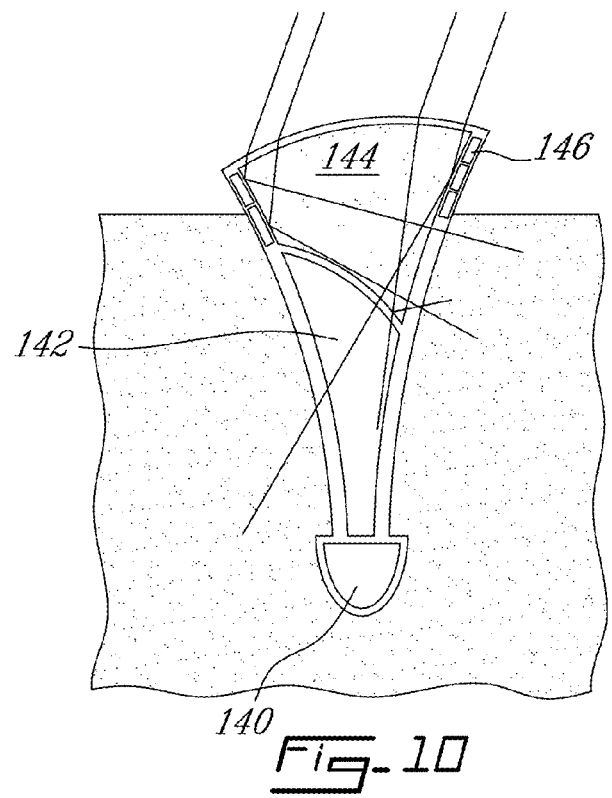
FIG. 10 shows a V-shaped structure with a perforated channel at its bottom for transport and distribution of gas, a dry air channel and a channel for a transparent liquid.

As shown in FIG. 10, the V-shaped structure can be made of extruded plastic material and can be shaped to include a few useful features. For example, a perforated channel for transport and distribution of air and/or $CO_2$ can be provided at the bottom of the V-shaped structure 140. A dry air channel 142 having a shape adapted for floatation is also provided. Pressurized air could be provided in dry air channel 142 to help compensate for hydrostatic pressure. A channel for a transparent liquid 144, for example water with facultative additives can also be provided. Air cavities 146 can be created in the walls of the V-shaped structure to facilitate total internal reflection within the V-shaped structure.

Figure 11:
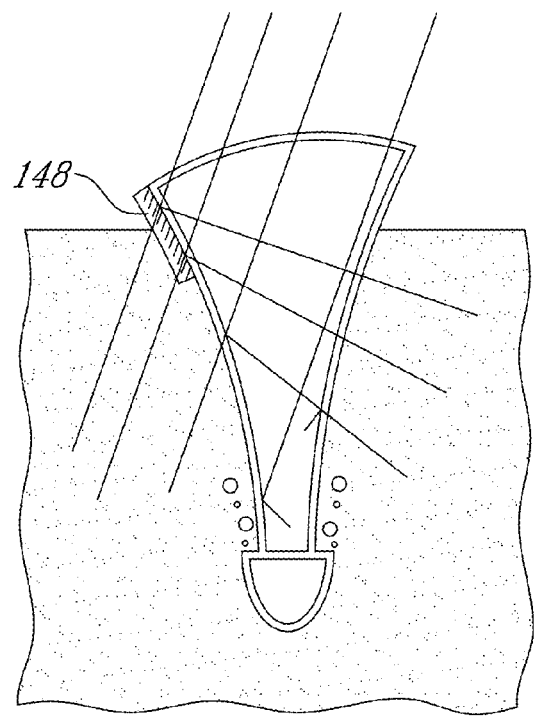
FIG. 11 shows a mirror affixed to the top of the exterior wall of the V-shaped structure.

As shown in FIG. 11, a mirror 148 can be affixed or provided at the top of the exterior surface of the V-shaped structure to facilitate reflection within the V-shaped structure. The reflector can be a sheet of aluminum with a coating of silver which can extend above and/or below the surface of the aqueous liquid.

Multiple light distributors which may or may not be identically sized and shaped, can be provided in the aqueous system such that the light entry surface of adjacent light distributors covers most of the open-ended surface of the system.

As will be readily understood, at some latitudes and for some algae concentrations in the aqueous liquid, it may be preferable to have narrower V-shaped structures, for which the width of the light entry surface is reduced and the height of the light distribution walls from the light entry surface to the bottom of the V-shaped structure is increased.

Simulations were carried out to determine the difference in light dilution between an open-ended photo bioreactor without solar tracking light distributors and one with solar tracking light distributors. FIG. 12 shows the penetration of light for a V-shaped light distributor. In FIG. 12A, the results are shown for system without light distributors. In FIG. 12B, the system includes light distributors. As shown in FIG. 12A, most of the sunlight is absorbed in a thin layer at the top of the photo bioreactor and the light intensity in that layer is at least one order of magnitude above the optimal value for efficient algae production. FIG. 12B shows that the light distributors distribute the sunlight in a much larger volume of aqueous liquid and that most of the volume is illuminated with an intensity closer to the optimal value.

A displacement system allows changing the orientation of the light entry surface of the multiple light distributors in the photo-bioreactor to allow tracking of the position of the sun. The displacement system allows proper positioning of the light entry surface of each light distributor generally towards the sun, depending on its current position. This displacement system can be individual for each light distributor or can be a global displacement system which controls a plurality of light distributors or all of them. The displacement system displaces the light distributors along at least one axis.

An example displacement system is shown in FIGS. 13A (summer) and 13B (fall). In this example displacement system 200, each V-shaped structure 202 is attached to two elongated rods 204, 206. The rods 204, 206 are displaced by a handle 208 which is also attached to the two elongated rods 204, 206. The movement of the handle 208 displaces each rod 204, 206 in an opposite direction and therefore forces the V-shaped structures 202 to pivot. The movement of the handle 208 can be controlled by an actuator.

The handle can receive a manual input to change the orientation of the light distributors or the actuator can use sensors and a controller to detect the position of the sun and orient the light distributors automatically and accordingly. The controller can provide an actuation command for the actuator(s). The controller may use stored solar position data to prepare the actuation command. For example, tables including the solar position for the time of day and day of year can be used by the controller. The controller may receive a manual input from a user to prepare the actuation command. The actuator(s) may also directly receive a manual input from a user to displace the light distributors. Feedback signals can be used to adjust the position and/or the position can be preprogrammed according to sun inclination projection data.

Figure 13:
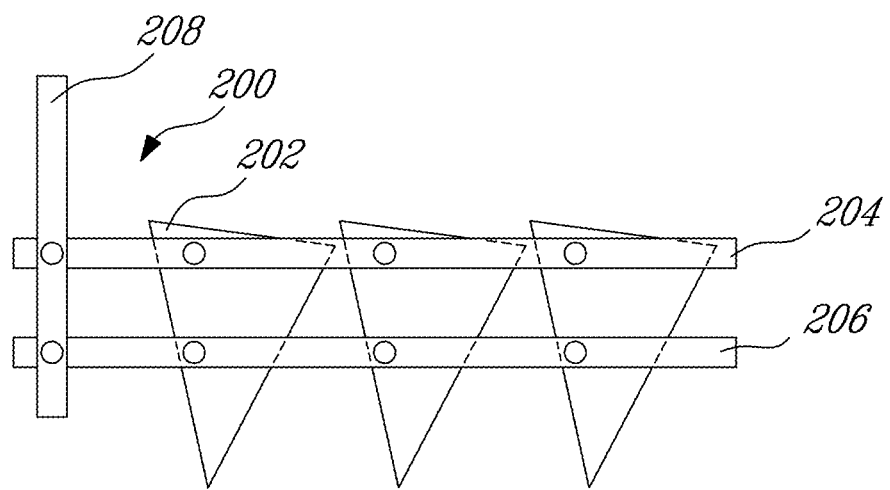
Figure 13:
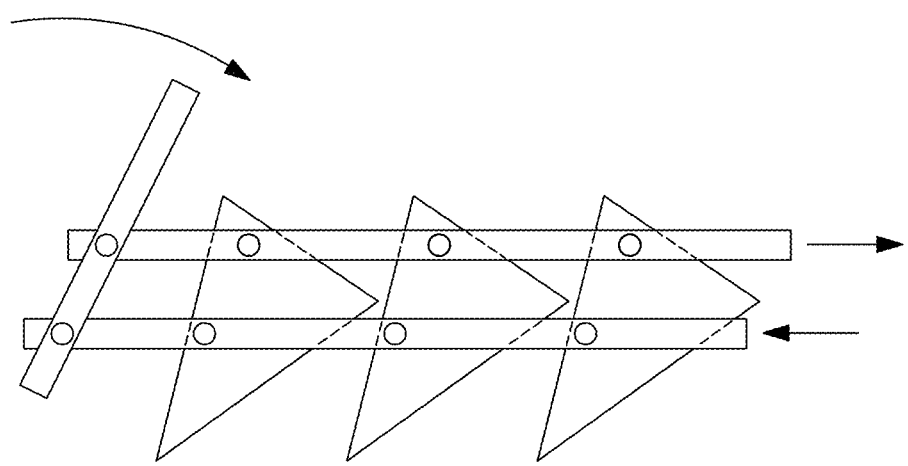
Figure 14:
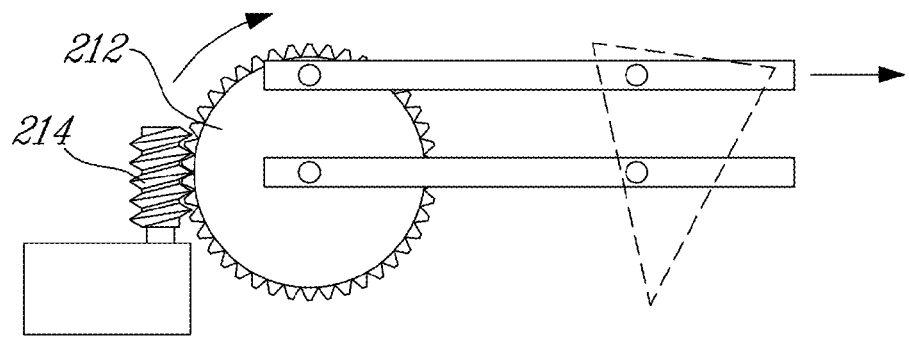
FIG. 14 shows a gear arrangement to orient the light distribution walls.

FIG. 14 shows a gear arrangement 212, 214 which is a variant to the handle of FIG. 13.

Figure 15:
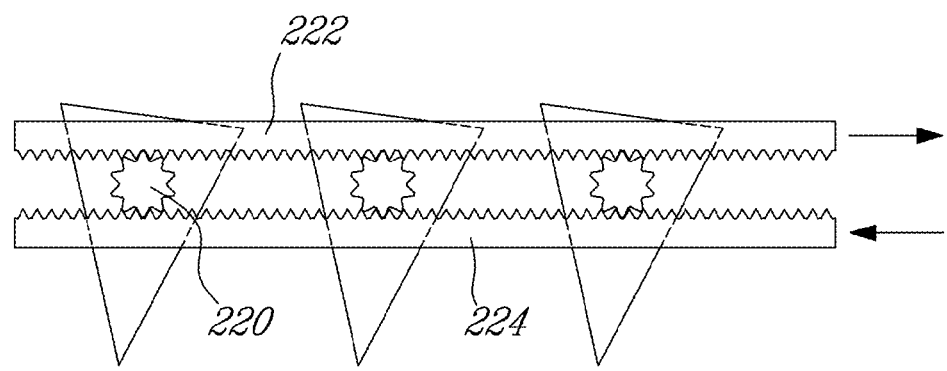
FIG. 15 shows a variant displacement system in which the light distributors are made to rotate via an individual gear which is rotated by dented rods.
Figure 16A:
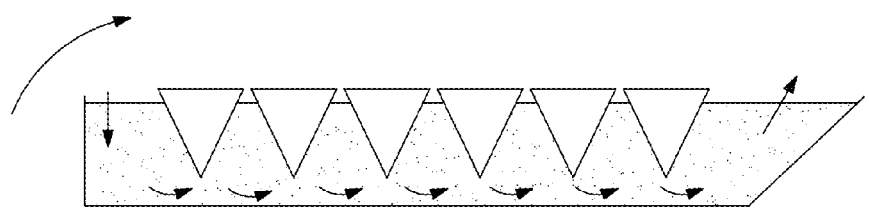
FIG. 16 includes FIG. 16A to 16E which show different methods to displace the aqueous liquid in the basin and therefore to displace the algae from one end of the basin to the other.
Figure 16B:
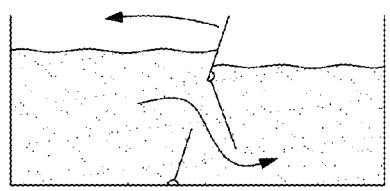
Figure 16C:
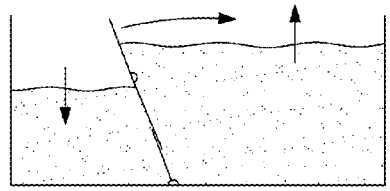
Figure 16D:
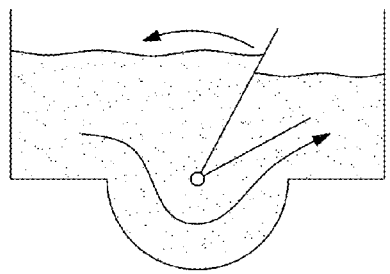
Figure 16E:
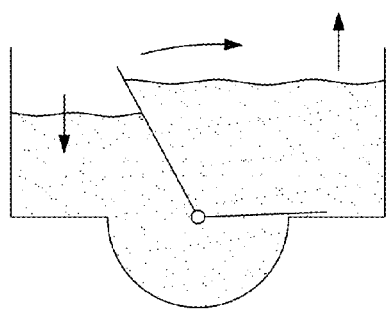
Figure 17:
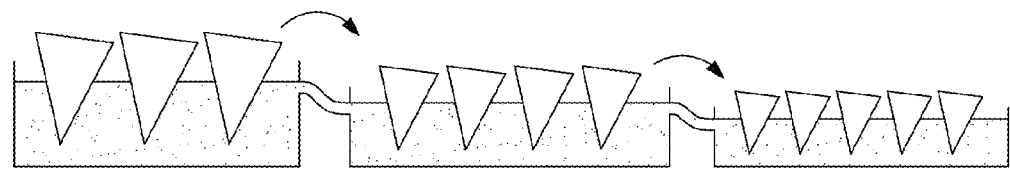
FIG. 17 shows a basin structure with multiple basins of varying sizes.

FIG. 15 shows a variant displacement system in which the light distributors are made to rotate via an individual gear 220 which is rotated by dented rods 222, 224.

Mechanical equivalents which allow to change the inclination of the light distribution walls will be known by the person skilled in the art.

As will be readily understood, the tracking may be approximate, within a precision range acceptable for the application. It is not necessary to fully track the position of the sun to benefit from light distribution improvement. The improvement in light dilution in the photo-bioreactor will be dependent on the actual percentage of light captured and distributed in the volume of aqueous liquid by the light distributors.

As will be understood, it may be determined that the photo-bioreactor algae production is inefficient in winter and is simply paused until spring.

It will also be understood that it may be advantageous to displace the algae to create a flow in the photo-bioreactor, allowing to continuously add water and nutrients after extracting some algae. It has been found that slow macro movements are preferable to rapid micro movements in order to avoid breaking the algae structure. Consequently, the photo-bioreactor may be shaped to allow a periodical displacement of the aqueous liquid with the algae and the light distributors may be installed in a manner facilitating this displacement and allowing the algae to travel, thereby benefiting from the light distribution of each light distributor which may, for any number of reasons, have varying light dilution factors. FIG. 16 shows different methods to displace the aqueous liquid in the basin and therefore to displace the algae from one end to the other using rotatable panels.

As will be readily understood, at the beginning of the production, the algae are in lesser concentration and the light dilution is high. Therefore, light distributors with large light entry surfaces in deep basins may be used. As the production progresses, light distributors with smaller light entry surfaces may be more appropriate and shallower basins may be used. At the end of the production, light distributors with small light entry surfaces are preferable in shallow basins. It may therefore be appropriate to create a basin structure which allows the algae to be transferred from one basin to the next according to its production status and in which the light distributor shape and basin size is adapted to the production status. This is shown schematically in FIG. 17.

Figure 24:
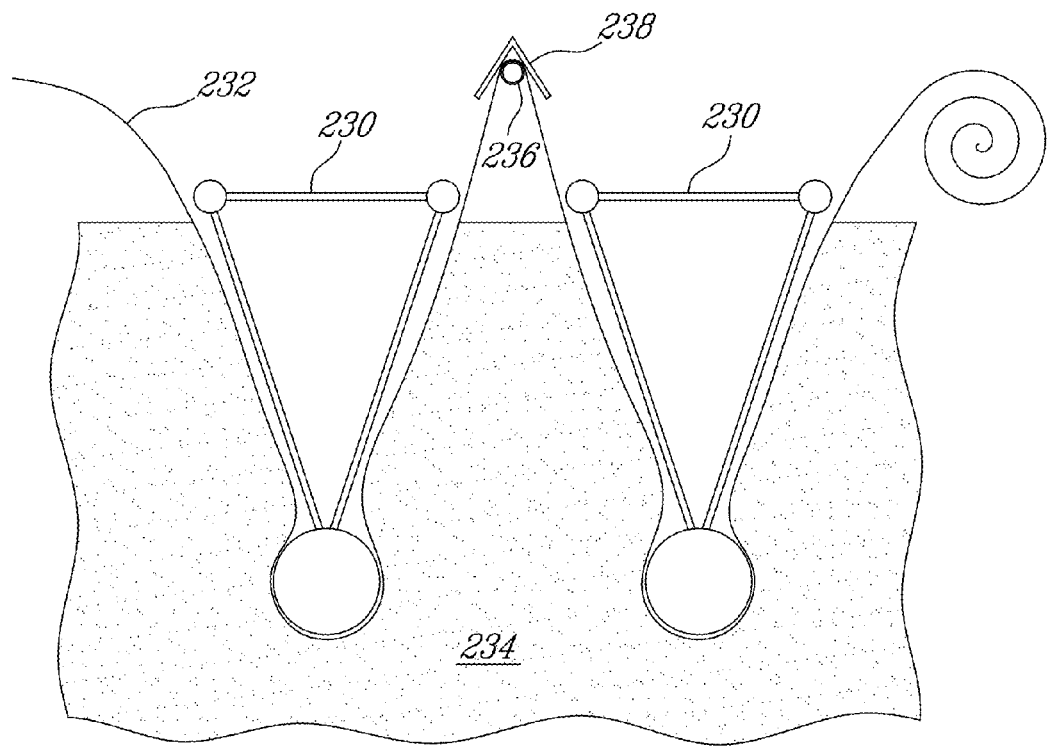
FIG. 24 shows a weighted rigid V-shaped structure provided in an open-ended basin with a sheet of thin film maintained at the interface between the rigid V-shaped structure and the aqueous liquid.
Figure 25:
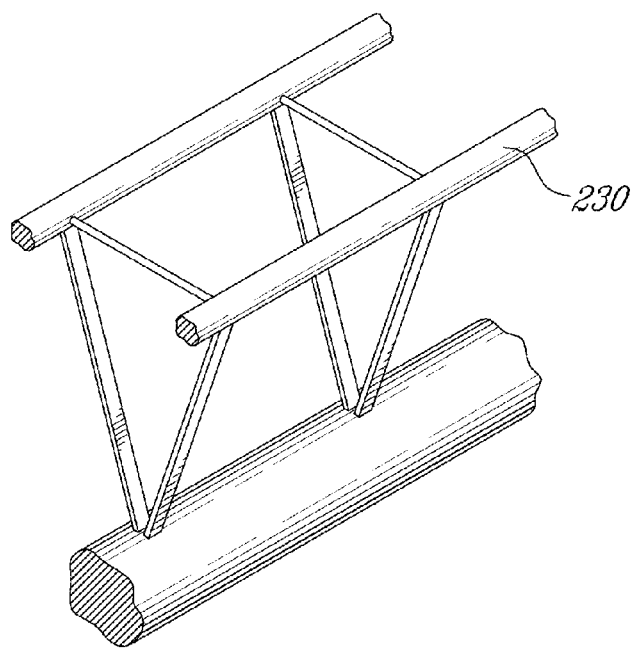
FIG. 25 shows a perspective view of the V-shaped structure of FIG. 24.

Another alternative embodiment for the light distributors to be used in open-ended basins is shown in FIGS. 24-25. As shown in FIG. 24, a weighted rigid V-shaped structure 230 is provided in an open-ended basin. This weighted rigid V-shaped structure can be made of metal or plastic. A sheet of thin film 232 is maintained at the interface between the rigid V-shaped structure 230 and the aqueous liquid 234 and is shaped by the structure to take on a V-shape. A rod 236 provided between adjacent rows of the V-shaped structure allows to maintain the film in between the rows. A reflector 238 can be provided on this rod 236 to redirect sun rays towards the V-shaped channel. FIG. 25 shows a perspective view of the V-shaped structure 230. The sheet of thin film 232 can be replaced periodically.

Figure 26:
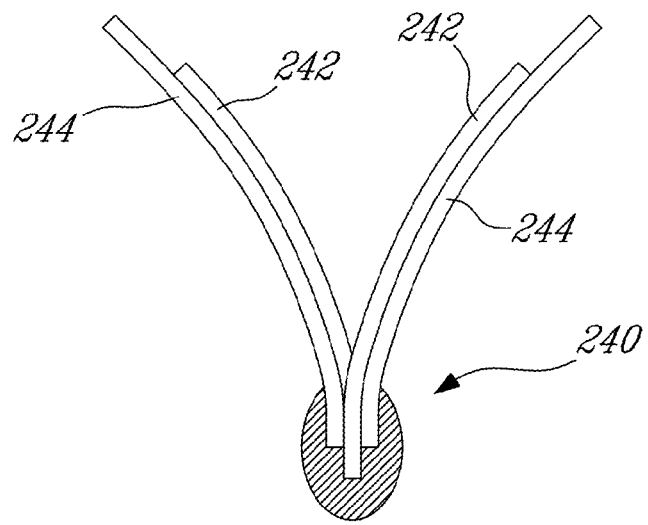
FIG. 26 shows an armature with transparent walls to create V-shaped surfaces.
Figure 27:
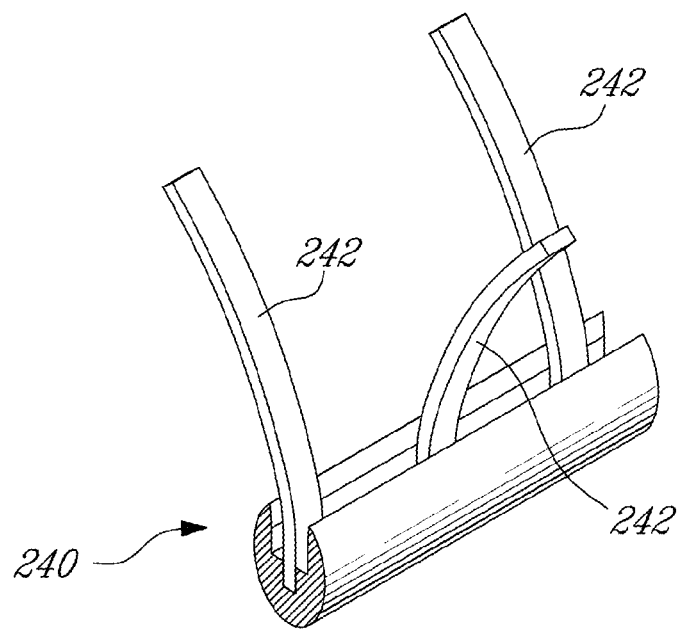
FIG. 27 shows a perspective view of the armature of FIG. 26.
Figure 28:
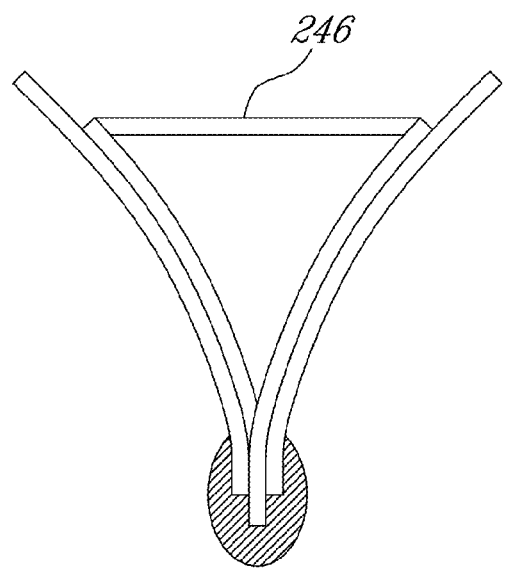
FIG. 28 shows an alternative to FIG. 26 in which a transversal rod is provided.
Figures 29, 30:
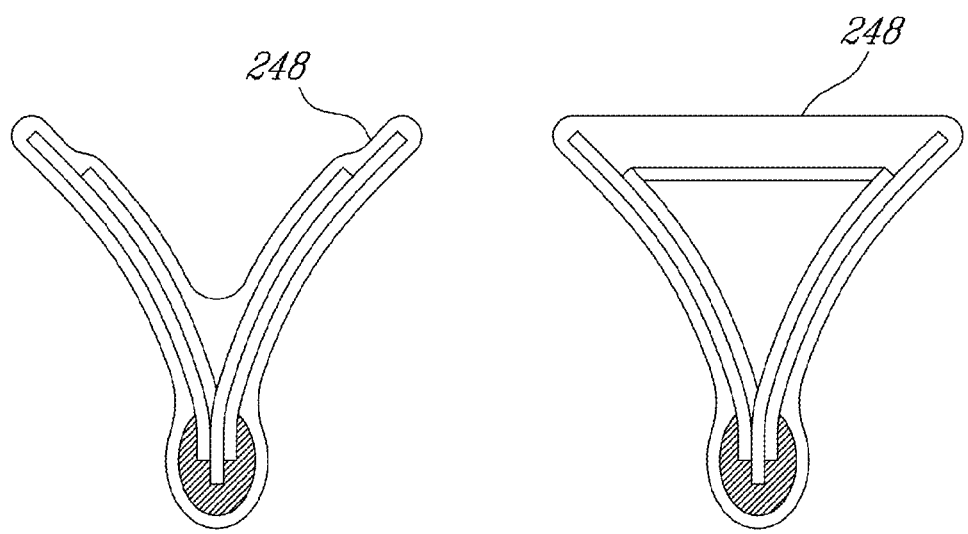
FIG. 29 shows the assembly of FIG. 26 with a thin film applied to the exterior wall.
FIG. 30 shows the assembly of FIG. 28 with a thin film applied to the exterior wall.

Still another alternative embodiment is shown in FIGS. 26-30. In this embodiment, a V-shaped structure 240 with a weighted base is provided in the basin. A strong armature 242 can give the V-shaped structure its shape and stability while transparent sheets of material 244, such as Poly(methyl methacrylate) (PMMA), are provided to create the V-shaped surfaces. FIG. 26 shows the assembled structure with the interior armature and the exterior layer of transparent material. FIG. 27 shows a perspective view of the armature. In FIG. 28, a transversal rod 246 is provided to solidify the structure. A thin film 248 can be applied to the exterior surface of the assembled V-shaped structure as shown in FIGS. 29 and 30.

Figure 32:
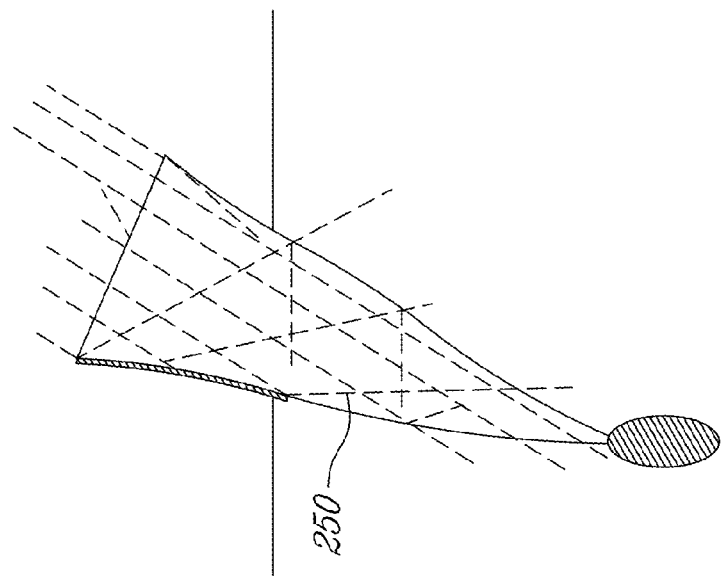
FIG. 32 shows the reflections of the sun rays for the V-shaped structures of FIG. 31.
Figure 31:
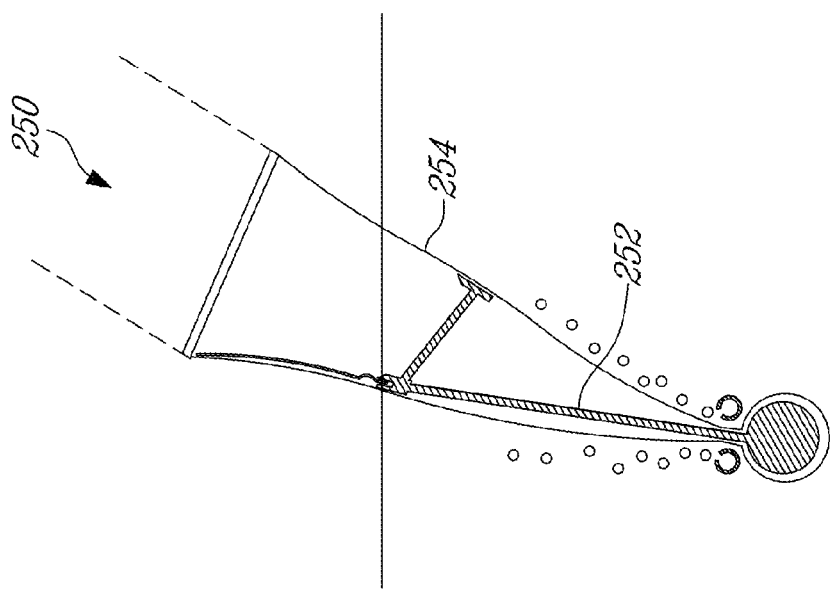
FIG. 31 shows an example V-shaped structure.
Figure 34:
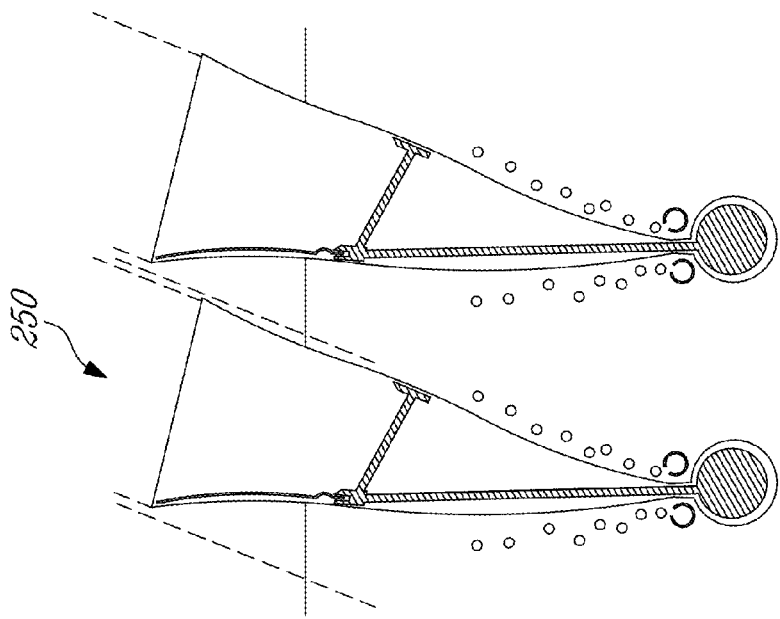
FIG. 34 shows the V-shaped structures of FIG. 31 oriented to track the sun in the summer months.
Figure 33:
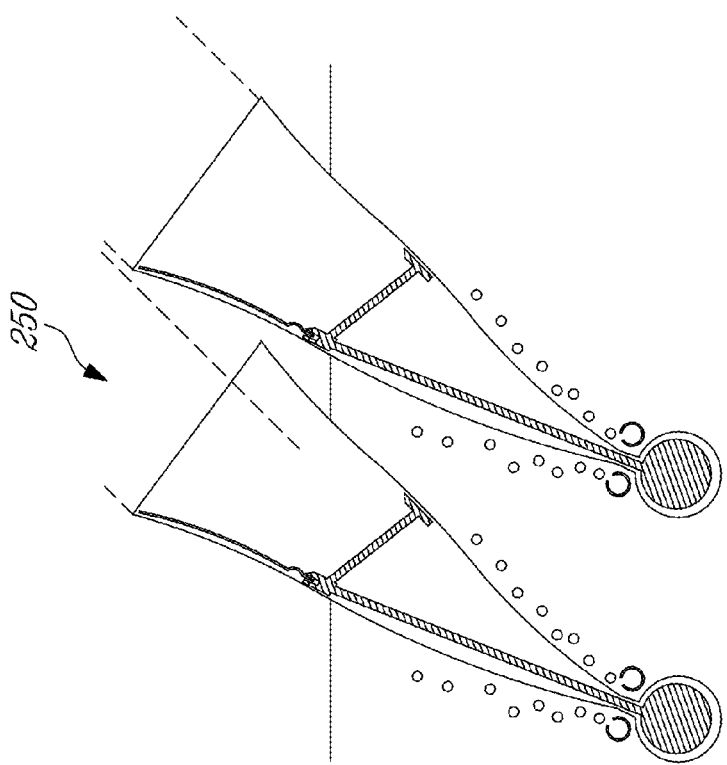
FIG. 33 shows example V-shaped structures of FIG. 31 oriented to track the sun at the Spring and Fall equinoxes.

FIGS. 31 to 37 show other example embodiments for the light distributors to be used in open-ended basins. FIG. 31 shows an example V-shaped structure 250. The V-shaped structure includes an armature 252 and a layer of transparent material 254. FIG. 32 shows the reflections of the sun rays for an example V-shaped structure. FIG. 33 shows example V-shaped structures of FIG. 31 oriented to track the sun at the Spring and Fall equinoxes and FIG. 34 shows the V-shaped structures of FIG. 31 oriented to track the sun in the summer months. In FIG. 31, the light entry surface has a width of 21 cm while the light distribution walls extend at least 10 cm above the surface of the aqueous liquid. The light distribution wall extends 35 cm below the surface of the aqueous liquid. There is a distance of 2 cm between adjacent V-shaped structures.

Figure 37:
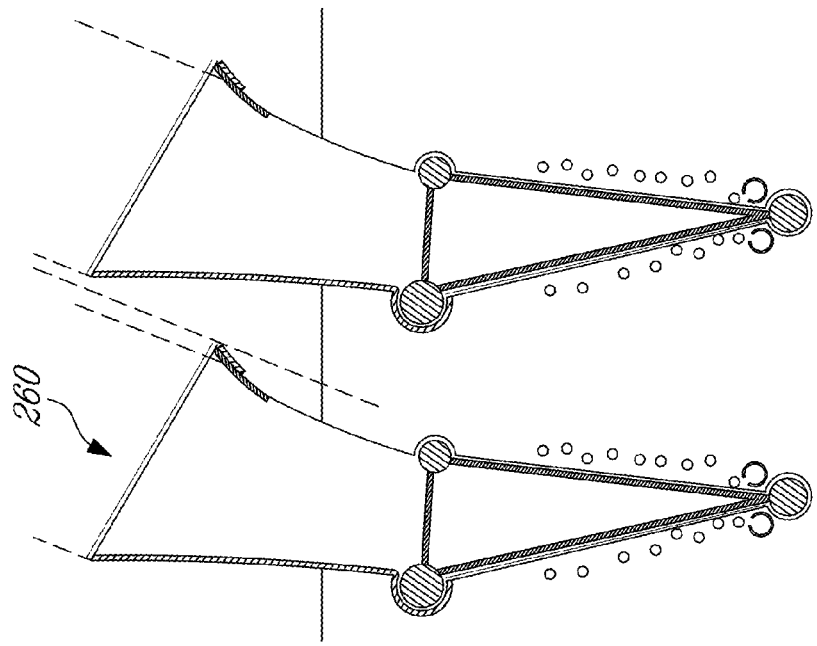
FIG. 37 shows the example V-shaped structure of FIG. 35 oriented to track the sun in the summer months.
Figure 36:
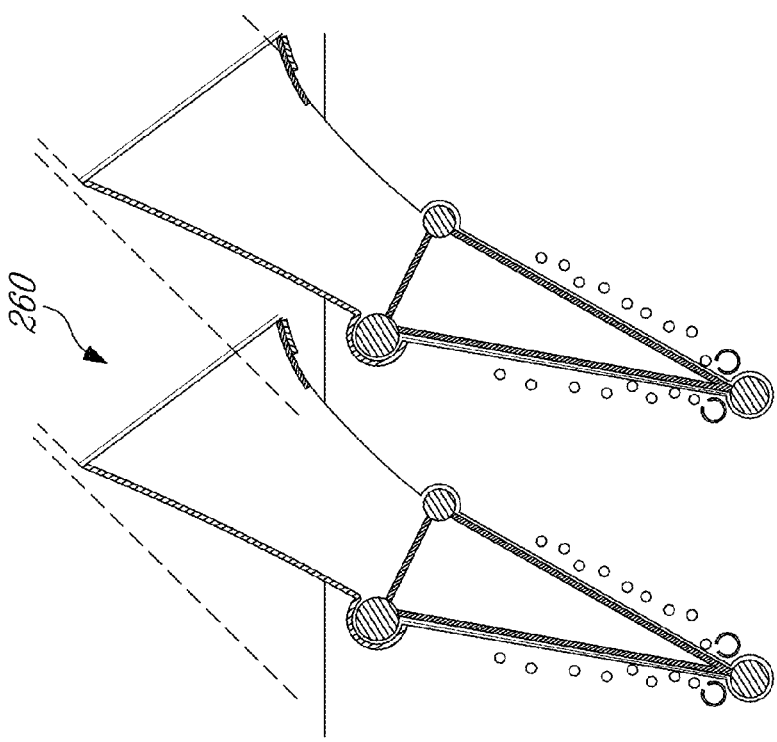
FIG. 36 shows the example V-shaped structure of FIG. 35 oriented to track the sun at the Spring and Fall equinoxes.

FIG. 35 shows an example V-shaped structure 260 with an internal triangular structure 262. An additional mirror 272, for example, made of a sheet of aluminum which can be coated with silver, is provided on the top of the most inclined light distribution wall 274 of the V-shaped structure 260. FIG. 36 shows the example V-shaped structure of FIG. 35 oriented to track the sun at the Spring and Fall equinoxes. FIG. 37 shows the example V-shaped structure of FIG. 35 oriented to track the sun in the summer months. In FIG. 35, the top of the V-shaped structure is provided at 26 cm above the surface of the aqueous liquid. There is a distance of 4 cm between adjacent V-shaped structures.

For closed systems, such as a PBR, elongated conduits 302 are shaped and juxtaposed to create a V-shaped region 310 between the rows of conduits 302. See FIGS. 4A, 4B and 4C. The elongated conduits are made of a thin transparent material and the aqueous algae culture occurs within the conduits. The elongated conduits are pulled from the top, creating substantially flat sides. The sides of the adjacent elongated conduits therefore act as the light distribution walls and the solar rays are able to be distributed within the conduits.

When the photosynthetic culture is in a closed photo-bioreactor, the light distribution walls are sidewalls of an elongated tube. In one embodiment, the elongated tube can be disposed in a S-shape so as to create a plurality of rows of the elongated tube. In another embodiment, elongated tubes are positioned to be adjacent and to form rows of elongated tubes. Manifolds are provided to interconnect the tubes.

The V-shaped channel is created by adjacent light distribution walls of adjacent rows of the elongated tube. The elongated tube includes a bottom wall to contain the photosynthetic culture between exterior sides of the light distribution walls.

The V-shaped channel is closed if the adjacent light distribution walls converge and meet at the bottom end. The V-shaped channel is open if the light distribution walls do not touch at the bottom end but are oriented such that imaginary extensions of the adjacent light distribution walls converge to meet at an imaginary point lower than the bottom end. The bottom wall and the light distribution walls can be made of a single sheet of transparent material.

The rows of elongated tubes need not be strictly parallel or straight. As will be readily understood, if a flexible material is used for the elongated tubes, the light distribution walls may not be strictly straight and the bottom end of the channel may have a varying width along the longitudinal axis of the elongated tube. The light distributors walls can be asymmetrical. The light distribution walls may have different lengths.

Referring back to FIG. 4A, FIG. 4B and FIG. 4C, for closed systems, such as a PBR, elongated conduits or tubes are shaped and juxtaposed to create a V-shaped region between the rows of conduits. The elongated conduits are made of a thin transparent material and the aqueous algae culture occurs within the conduits. The elongated conduits are pulled from the top. The sides of the adjacent elongated conduits therefore act as the light distribution walls and the solar rays are able to be distributed within the conduits. The walls of the tubing are the interface between the outside environment and the volume of aqueous liquid. The tubing walls can be oriented such that they follow the solar inclination throughout the year.

It will be readily understood that the resulting V-shaped structures between the rows of conduits have optical properties which are similar to that of the V-shaped structure of FIG. 2, namely the open-ended V-shaped structure.

Figure 4A:
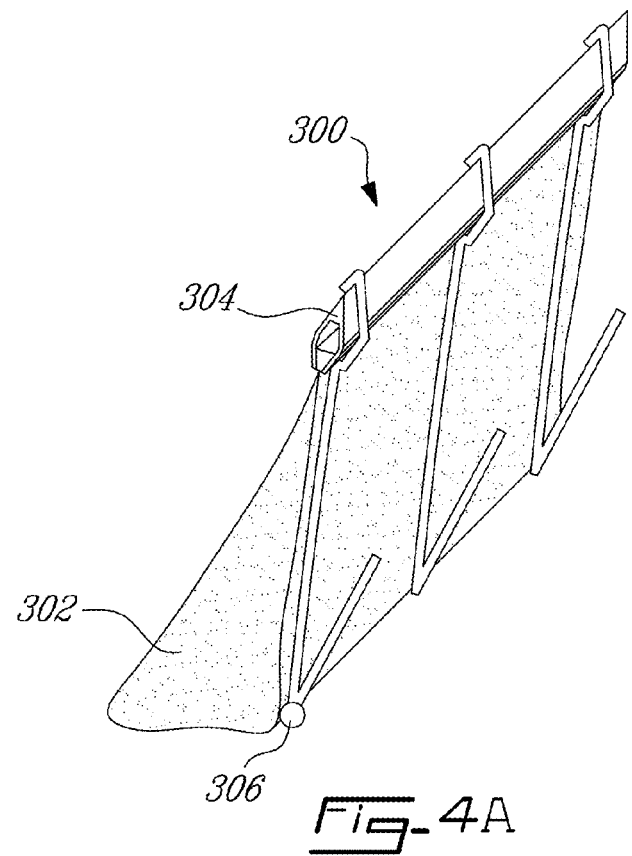
FIG. 4A shows an elongated tube or conduit for the transport of aqueous liquid.
Figure 4B:
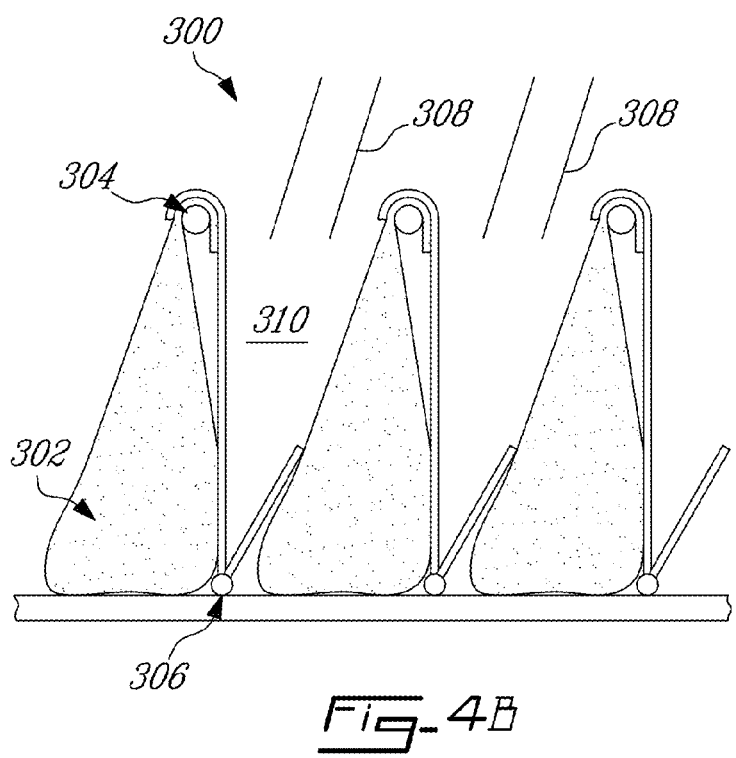
FIG. 4B shows a side view of the system with a plurality of adjacent rows of tubes of the type of FIG. 4A

In an example embodiment shown in FIG. 4B, the light distribution tubing system 300 includes an elongated tube 302, mechanical attachment means 304 and a displacement system with pivot 306 for participation in adjusting an angle of the tube depending on the solar inclination.

The elongated tube 302 is made of at least one sidewall. In one embodiment, it is made of a flexible thin material. The flexible material can be a polymer pellicle made up at least one layer. For example, thin plastic sheets can be used to form the tubing, similar to those used in the manufacturing of milk bags. Layers of these thin plastic sheets can be stacked with different optical, physical or biological properties to provide an ideal environment for the culture of the vegetal species. For example, in tubing made of three layers of polymers, an external layer can be UV-resistant or even UV-filtering, a middle layer can be significantly mechanically resistant and the internal layer can have a low adherence to the components present in the aqueous liquid.

In another embodiment, the elongated tube can be made of a rigid material. It can be an extruded polymer tube, for example.

Figure 18A:
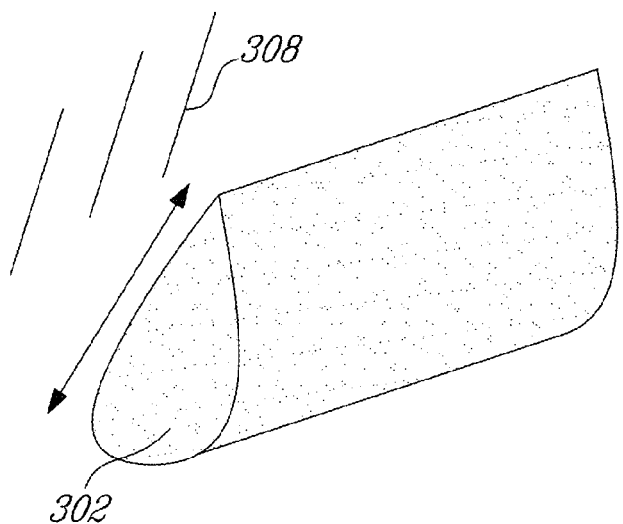
FIGS. 18A, 18B show the effect of the displacement system on the shape and angle of the tubing.
Figure 18B:
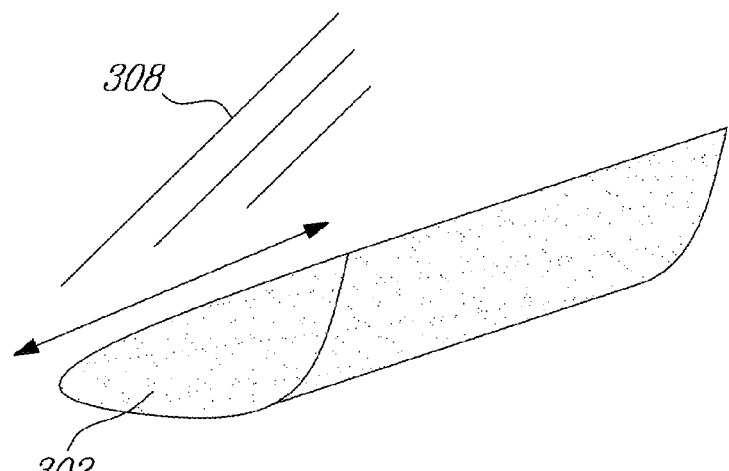

FIGS. 18A, 18B show the effect of the displacement system on the shape and angle of the tubing 302. The angle of both walls changes with the displacement of the attachment means and the wall is thereby adapted to capture sunlight 308 coming from different angles.

Figure 19A:
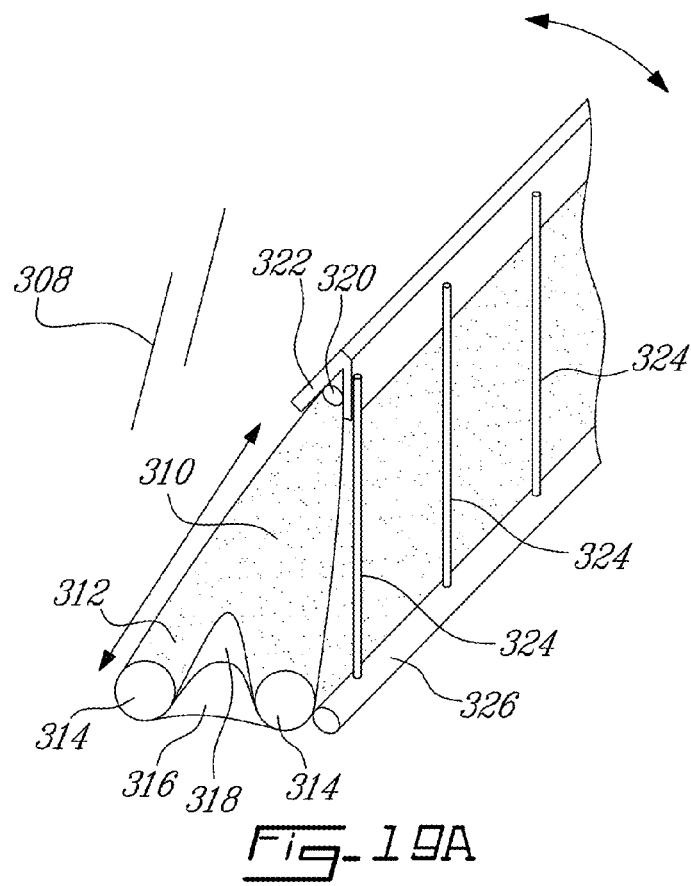
FIGS. 19A, 19B show an example tubing provided with internal channels and a holding structure.
Figure 19B:
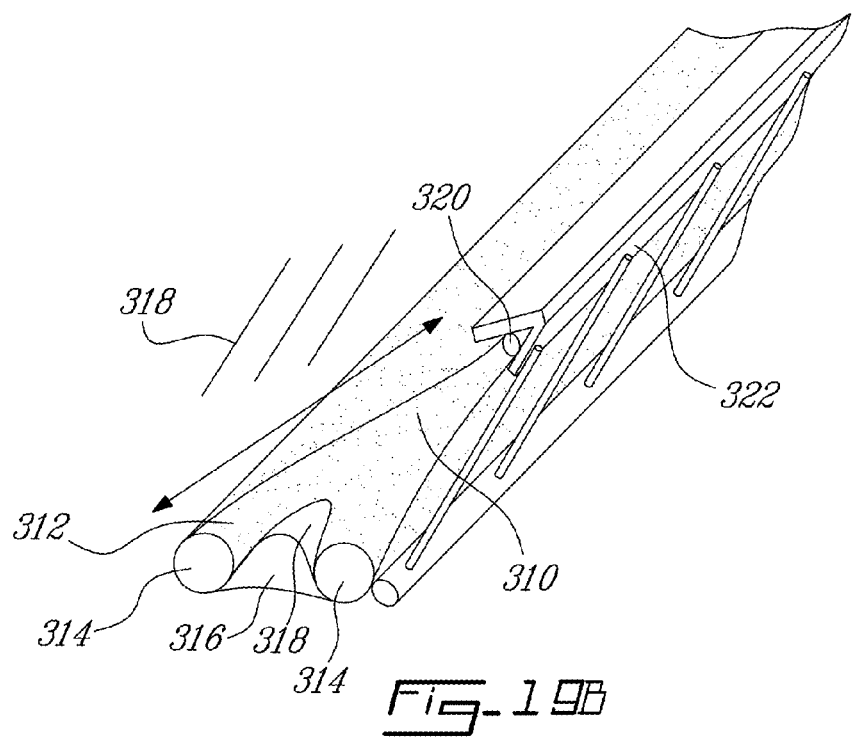

In an example tubing provided with internal channels, such as tubing 310 shown in FIGS. 19A, 19B, one channel 312 can be used to transport the plant and aqueous liquid, for example the algae in water, one channel 314 can transport carbon dioxide and distribute it to the algae channel along the way, one channel 316 can transport clear water to help shape the tubing in an appropriate shape or to create thermal communication with the ground surface, one channel 318 can transport air to create insulation or again to help with the shape of the tubing, etc.

The mechanical attachment means 320 attach the elongated top surface of the elongated tube to a support 322. The attachment means exert an upward force on the elongated tube to give it an upward pointing shape, a triangular shape, which pulls on the sidewall to give an angle to both sides, this angle being adapted for solar tracking. Furthermore, this triangular shape allows capturing the light and keeping most of it within the tube. The support 322 can include vertical rods 324 and a pivot 326.

Figure 20:
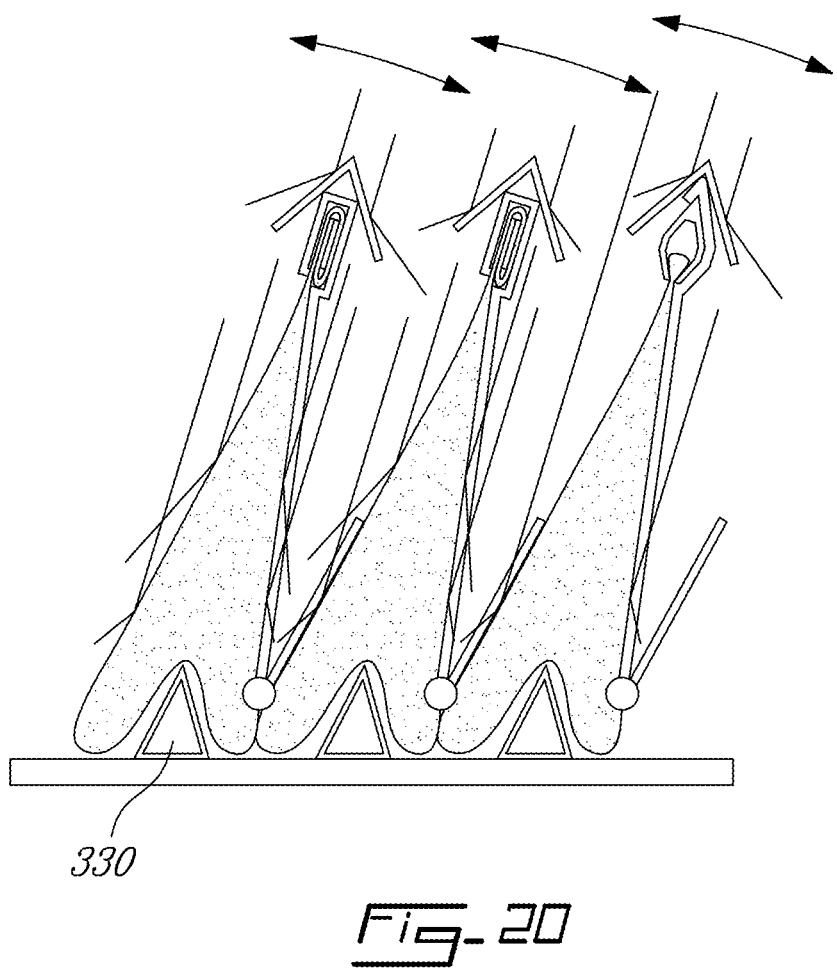
FIG. 20 shows an example tubing with a mechanical structure to give a shape to the tubing.

As shown in FIG. 20, a mechanical structure 330, having a triangular shape in this case, can be used to give a shape to the tubing.

Figure 21A:
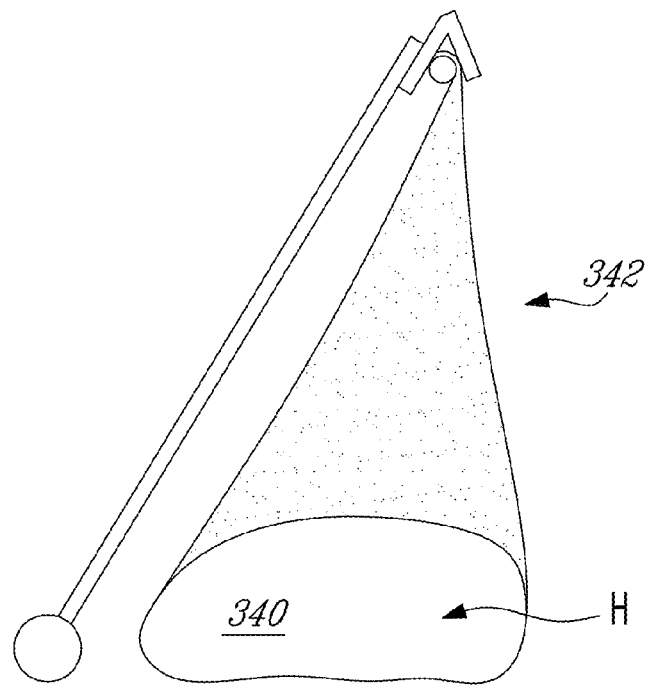
FIG. 21 includes FIG. 21A and FIG. 21B in which an example tubing with a pressurized air/water channel which controls the shape of the algae channel is shown with a high pressure channel in FIG. 21A and a low pressure channel in FIG. 21B.
Figure 21B:
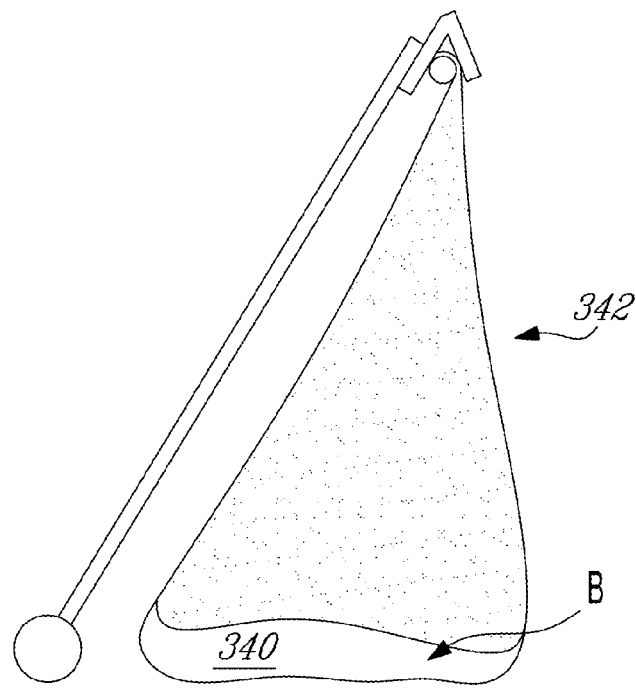

As shown in FIG. 21, the channels created in the elongated tube can allow regulating the quantity of aqueous liquid in the tubing. This can be useful to allow a lesser quantity of algae to circulate in the channel when the sun is at a lower angle. A pressurized air or water channel 340 is provided at the bottom of the tubing 342 and, as shown in FIG. 21A, if the pressurized air or water is at a high pressure (H), it will reduce the size of the aqueous liquid channel. As shown in FIG. 21B, if the pressurized air or water channel is at low pressure (B) it will increase the size of the aqueous liquid channel.

In another embodiment, not shown, the aqueous liquid can circulate in a channel surrounded by two channels which have a different pressure, the size and shape of the surrounded channel will be affected by the pressure in each surrounding channel and the volume of aqueous liquid will be modified.

Figure 22:
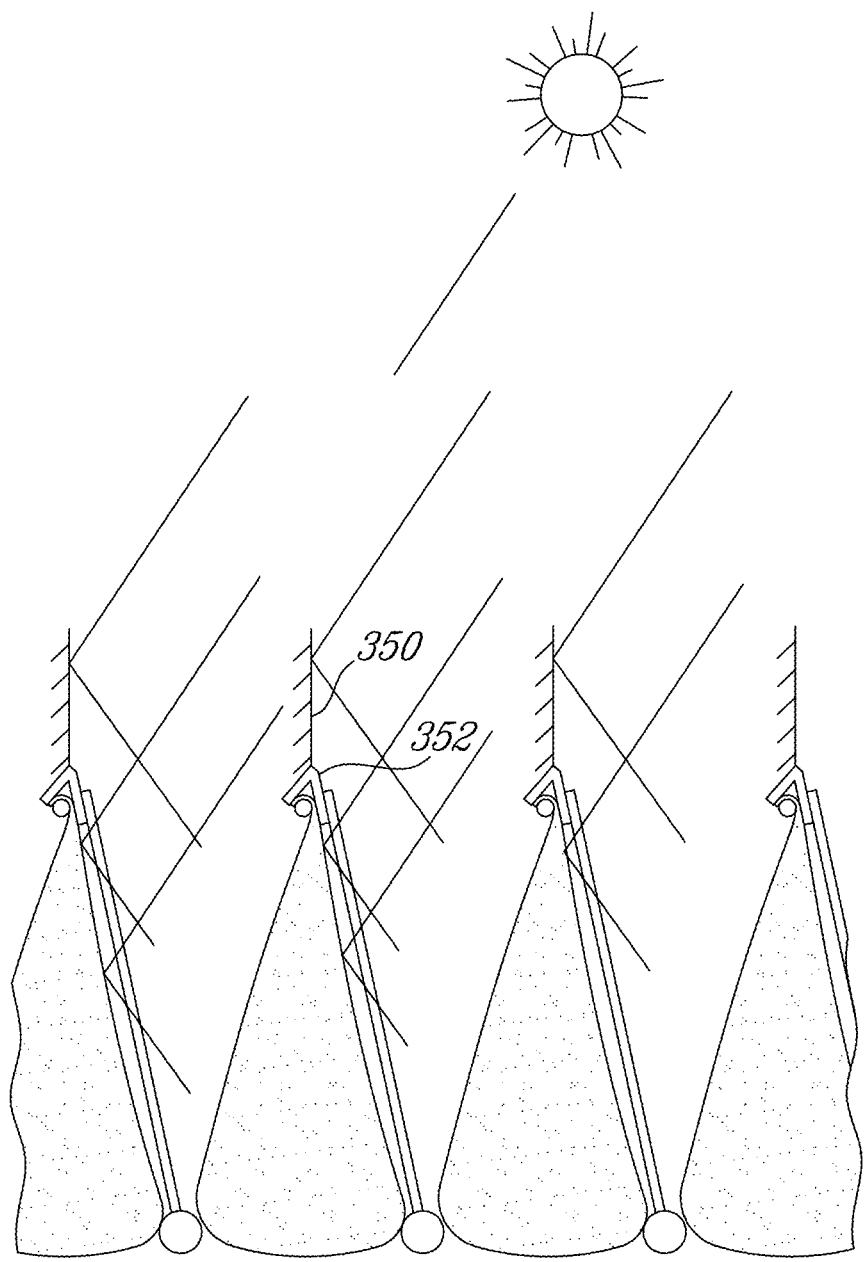
FIG. 22 shows a mirror affixed to the top of the attachment structure.

As shown in FIG. 22, a mirror 350 can be affixed to the top of the attachment structure 352 to redirect light towards shaded portions of the V-shaped space between the rows of tubing. It facilitates reflection within the V-shaped channels.

Figure 23:
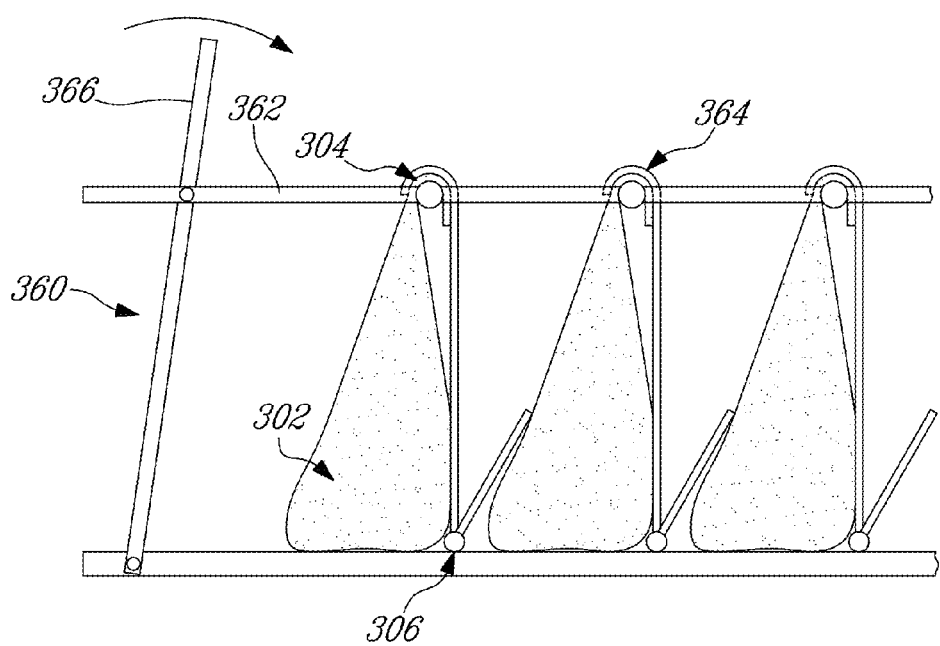
FIG. 23 shows a displacement system for the elongated tube.

FIG. 23 shows a displacement system 360 for the elongated tube embodiment of FIG. 4. Pivot 306 is fixed and a rod 362 is attached to the top end of the structure 364 at attachment 304. The handle 366 is displaced to allow displacement of the elongated tubes.

Figure 4C:
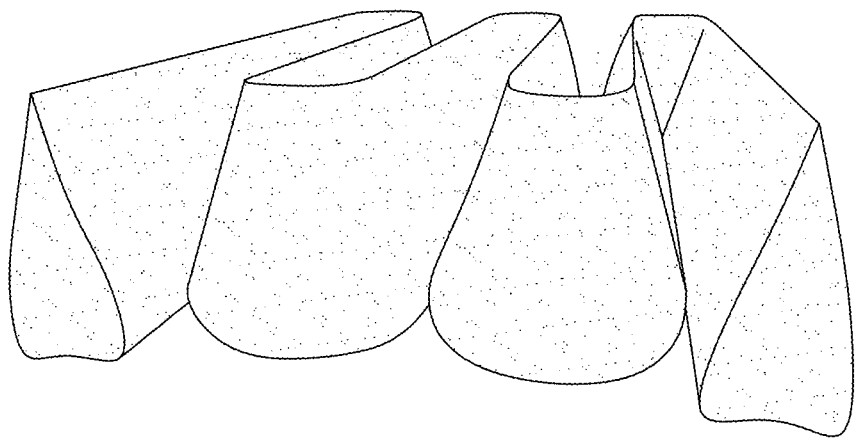
FIG. 4C shows a perspective view of the rows of elongated tubes without the support system to show an example positioning of the tubes on the ground.

As will be readily understood, the elongated tubing can be provided in a compressed S-configuration on the ground such as the snaking arrangement shown in FIG. 4C. The ground can be wet to improve thermal conduction. The elongated tubing can also be disposed in basins with a low depth which can contain liquid, such as water, for example to increase the thermal conduction.

As will be readily understood, V-shaped and parallelogram-shaped light distribution channels may have irregular walls and as such, the shape of the V and the shape of the parallelogram may be approximate. The use of the words "V" and "parallelogram" is for ease of description and should not be construed as limiting the actual physical shape or rigidity of the walls, the cross-section and/or the volume of the light distribution channel.

It will be readily understood that the displacement system may affect the cross-sectional shape of the light distribution channel as it is orienting the walls for sun-tracking.

It will be readily understood that a parallelogram channel with irregular walls may take on a tetragonal shape with straight or irregular walls.

The embodiments described above are intended to be exemplary only. The scope of the invention is therefore intended to be limited solely by the appended claims.

We claim:

1. A sun-tracking light distributor system for use in a closed photo-bioreactor for a photosynthetic culture having an aqueous liquid, the distributor system comprising:
   two light distribution walls made of a transparent material allowing sunlight to pass therethrough, the two light distribution walls being facing sidewalls of adjacent sections of transparent tube, the tube being adapted to contain the aqueous liquid, the two light distribution walls creating an elongated channel with an interior space being provided by a spacing between the adjacent sections of tube and adapted to receive the sunlight;
   a displacement system operatively connected to at least one of the two light distribution walls, the displacement system being adapted to change an orientation of said at least one of the two light distribution walls to track a solar position with respect to at least one axis.

2. The sun-tracking light distributor system as claimed in claim 1, wherein the tube has one of a drop-shaped cross-section and an inverted V-shaped cross-section.

3. The sun-tracking light distributor system as claimed in claim 1, wherein the tube has one of a parallelogram cross-section and an obround-shaped cross-section.

4. The sun-tracking light distributor system as claimed in claim 3, wherein the tube is separated in upright sections, said upright sections defining a path for circulation of said aqueous liquid in said tube.

5. The sun-tracking light distributor system as claimed in claim 1, wherein each of said light distribution walls is formed by neighboring upright tubes disposed side-by-side along said elongated channel, and wherein said neighboring upright tubes are one of independent and solidary.

6. The sun-tracking light distributor system as claimed in claim 1, wherein said two light distribution walls are oriented to be provided at an angle at a bottom end thereby creating an elongated V-shaped channel, said elongated V-shaped channel being one of closed and open at said bottom end.

7. The sun-tracking light distributor system as claimed in claim 6, wherein said V-shaped channel is open at said bottom end and a bottom wall extending between bottom ends of said light distributions walls is provided.

8. The sun-tracking light distributor system as claimed in claim 1, wherein said two light distribution walls are oriented to create a parallelogram-shaped channel.

9. The sun-tracking light distributor system as claimed in claim 1, wherein the displacement system includes attachment means connected to said tubes to give at least one of an inclination, a shape, a rigidity and a support to at least one of said sidewalls.

10. The sun-tracking light distributor system as claimed in claim 1, wherein the tubes is made of a flexible material and wherein a shape of said light distribution walls is variable.

11. The sun-tracking light distributor system as claimed in claim 1, wherein the displacement system is adapted to change an inclination of the two light distribution walls with a single displacement operation.

12. A method for distributing light in a closed photo-bioreactor for a photosynthetic culture, comprising:
   providing a sun-tracking light distributor system as claimed in claim 1 in said closed photo-bioreactor; and
   changing an orientation of at least one of said light distribution walls using said displacement system to allow tracking of the sun.

* * * * *